United States Patent [19]

Mehra

[11] Patent Number: 4,696,688
[45] Date of Patent: Sep. 29, 1987

[54] CONVERSION OF LEAN OIL ABSORPTION PROCESS TO EXTRACTION PROCESS FOR CONDITIONING NATURAL GAS

[75] Inventor: Yuv R. Mehra, Odessa, Tex.

[73] Assignee: Advanced Extraction Technologies, Inc., Houston, Tex.

[21] Appl. No.: 828,996

[22] Filed: Feb. 13, 1986

Related U.S. Application Data

[63] Continuation-in-part of Ser. No. 808,463, Dec. 13, 1985, which is a continuation-in-part of Ser. No. 784,566, Oct. 4, 1985, Pat. No. 4,617,038, which is a continuation-in-part of Ser. No. 759,327, Jul. 26, 1985, Pat. No. 4,623,371, which is a continuation-in-part of Ser. No. 758,351, Jul. 24, 1985, Pat. No. 4,601,738, which is a continuation-in-part of Ser. No. 637,210, Aug. 3, 1984, Pat. No. 4,578,094, which is a continuation-in-part of Ser. No. 532,005, Sep. 14, 1983, Pat. No. 4,526,594, which is a continuation-in-part of Ser. No. 507,564, Jun. 24, 1983, Pat. No. 4,511,381, which is a continuation-in-part of Ser. No. 374,270, May 3, 1982, Pat. No. 4,421,535.

[51] Int. Cl.$^4$ ............................................. F25J 3/00
[52] U.S. Cl. ........................................ 62/17; 55/26; 55/68; 62/20
[58] Field of Search .................... 62/17, 20; 55/26, 68

[56] References Cited

U.S. PATENT DOCUMENTS

| | | | |
|---|---|---|---|
| 1,768,521 | 6/1930 | Ayres, Jr. ............................ | 55/48 |
| 1,953,043 | 3/1934 | Cole, Jr. et al. ................... | 196/8 |
| 2,290,957 | 7/1942 | Hachmuth ........................... | 196/8 |
| 2,321,666 | 6/1943 | Felbeck .............................. | 62/175.5 |
| 2,455,803 | 12/1948 | Pierotti ............................. | 203/58 |
| 2,620,895 | 12/1952 | Turner ............................... | 183/120 |
| 2,846,443 | 8/1958 | Malusa et al. ..................... | 260/326.5 |
| 2,868,326 | 1/1959 | Gilmore ............................. | 183/115 |
| 2,938,865 | 5/1960 | Moyer ............................... | 208/341 |
| 3,236,029 | 2/1966 | Afdahl et al. ..................... | 55/44 |
| 3,280,206 | 10/1966 | Scola et al. ...................... | 260/674 |
| 3,349,145 | 10/1967 | Uitti ................................ | 260/672 |

OTHER PUBLICATIONS

"Ethylene Purification by Absorption Process", by Kniel and Slager, *Chemical Engineering Progress*, vol. 43, No. 7, Jul. 1947, pp. 335-342.

"Propane Recovery by Absorption," by Ludwig Kniel in *Petroleum Refiner*, vol. 27, No. 11, Nov. 1948, pp. 108-113.

"Le Calcul des Absorbeurs a Fractionnement," by L. Kniel in *Bulletin de l'Association Francaise des Techniciens du Petrole*, No. 82, Aug. 1950, pp. 31-56.

"Petroleum Processing—Principles and Applications," by R. J. Hengstebeck, McGraw-Hill Book Co., New York, N.Y., 1959, pp. 56-64.

"Humble's Avery Island Plant: High Safety at Low Cost", by J. J. Weatherby, *Hydrocarbon Processing & Petroleum Refiner*, Apr. 1962, vol. 41, No. 4, pp. 113-116.

"Gas Absorption", as Chapter 8 in Mass Transfer Operations, by Treybal, McGraw-Hill Book Company, Second Edition, 1968, pp. 221-226 and pp. 393-395.

*Primary Examiner*—Ronald C. Capossela
*Attorney, Agent, or Firm*—Depaoli & O'Brien

[57] ABSTRACT

A continuous process for selective countercurrent extraction of $C_2+$ hydrocarbons from a gas stream with a lean oil as solvent is rejuvenated by substitution of a preferential physical solvent for the lean oil solvent to produce a residue gas stream meeting specifications for methane content and a hydrocarbon product having a composition which can be adjusted to a selected minimum degree for ethane that is as low as 2% ethane and produce at the maximum propane content that is available from the equipment, whereby profitability of the extraction operation can be maximized at all times. The preferential physical solvent has a minimum relative volatility of methane over ethane of at least 6.0 and a solubility of at least 1.0 standard cubic foot of gaseous hydrocarbons per gallon of the solvent (thereby defining its hydrocarbon loading capacity) or, alternatively, a preferential factor of at least 6.0. Preferred solvents include polyalkylene ethers of dialkylene glycol and alkyl-substituted monocyclic $C_8$-$C_{10}$ aromatic hydrocarbons, preferably including mesitylene, reformates, crackates, and mixed xylenes.

47 Claims, 4 Drawing Figures

OTHER PUBLICATIONS
(See top sheet)

"Chemical Engineers' Handbook", Ed. by John H. Perry, McGraw-Hill Book Company, Fourth Edition, 1969, pp. 13-46 and 13-47.

"High $CO_2$–High $H_2S$ Removal with Selexol Solvent," by John W. Sweny, 59th Annual GPA Convention, Mar. 17-19, 1980, Houston, Texas.

"Gas Conditioning," Under Natural Gas in vol. 11 of *Kirk-Othmer Encyclopedia of Chemical Technology*, Third Edition, 1980, pp. 638-641.

"Absorption" Under Liquified Petroleum Gas in vol. 14 of Kirk-Othmer Encyclopedia of Chemical Technology, Third Edition, 1980, pp. 383-388.

*Gas Processors Report*, Texas Coast, Spears Consulting Group, P.O. Box 33002, Tulsa, OK 74153, Oct. 14, 1985, pp. 1, 7 and 8.

CONVERSION OF LEAN OIL ABSORPTION PROCESS TO EXTRACTION PROCESS FOR CONDITIONING NATURAL GAS

RELATED APPLICATIONS

This is a continuation-in-part of co-pending application Ser. No. 808,463, filed Dec. 13, 1985, which is a continuation-in-part of application Ser. No. 784,566, filed Oct. 4, 1985, now U.S. Pat. No. 4,617,038, which is a continuation-in-part of application Ser. No. 759,327, filed Jul. 26, 1985, now U.S. Pat. No. 4,623,371 which is a continuation-in-part of co-pending application Ser. No. 758,351, filed Jul. 24, 1985, now U.S. Pat. No. 4,601,738, which is a continuation-in-part of co-pending application Ser. No. 637,210, filed Aug. 3, 1984, now U.S. Pat. No. 4,578,094, which is a continuation-in-part of application Ser. No. 532,005, filed Sept. 14, 1983, now U.S. Pat. No. 4,526,594, which is a continuation-in-part of application Serial No. 507,564, filed June 24, 1983, now U.S. Pat. No. 4,511,381, which is a continuation-in-part of application Ser. No. 374,270, filed May 3, 1982, now U.S. Pat. No. 4,421,535.

BACKGROUND OF THE INVENTION

1. Field of the Invention

This invention relates to contacting a natural gas stream with a preferential physical solvent. It more specifically relates to separating and recovering ethane, propane, and higher boiling hydrocarbons from natural gas streams and especially relates to rejuvenation of conventional lean oil absorption plants which recover hydrocarbons from a natural gas stream. It further relates to specific preferential physical solvents for recovery of selected hydrocarbons from a natural gas stream.

2. Review of the Prior Art

Hydrocarbons must often be recovered from such natural gas streams as natural gas, alkylates, reformates, and the like. Many recovery processes are available, but countercurrently contacting the upwardly flowing gas stream with a downwardly flowing liquid under conditions furnishing high interfacial surface area is often a preferred recovery process, generally known as absorption and herein identified as extraction when highly preferential physical solvents are used.

Most physical solvents show some preference among hydrocarbons in a mixture thereof. In other words, they have greater solvency, perhaps because of a stronger physical attraction, for one or more hydrocarbons in such a mixture. This preference is measured by the absorption principle, leading to an alpha or relative volatility. Most of the commonly used lean oils, for example, have relative volatilities of methane over ethane of slightly less than 5.

Each gaseous hydrocarbon goes into solution in the lean oil in inverse proportion to its vapor pressure, the lower the vapor pressure, the greater the tendency to dissolve, each component being concentrated as an "absorbate" dissolved in the lean oil. Absorption can also be increased within an absorption column by an increased flow rate of lean oil, by decreased temperature because the vapor pressures of the absorbed compounds are lowered, and by increased pressure because more absorbate is dissolved by raising the partial pressures of the absorbates.

Lean oils are usually high-boiling gasoline fractions or distillate-fuel stocks like kerosene which are chosen according to absorption capacity, lean oil loss, viscosity, and stability. Because absorption capacities of liquids are molal functions, lighter oils, which have lower molecular weights, have high absorption capacities on a weight basis. Any hydrocarbon oil has a greater capacity to absorb chemically similar materials, and most of the vapors to be absorbed from a natural gas are paraffinic; therefore, paraffinic lean oils are preferable for a natural gas. Loss of lean oil, which is inversely proportional to the molecular weight of the lean oil, must be balanced against the greater absorption capacity of a lower molecular weight oil.

The rate of mass transfer in absorption depends principally on the molecular weight and relative viscosity of the lean oil. Because higher rates of transfer are obtained when using less viscous, lower molecular weight oils, their use minimizes the tray packing requirements for a given operation.

It is pertinent to the invention that lean oils have been used for at least about 60 years in absorption plants which recover $C_4+$ hydrocarbons from natural gas streams. It is highly pertinent to this invention that the lean oils are non-selective for lighter hydrocarbons, such as methane, ethane, and propane, which represent most of a natural gas stream. The higher partial pressure in the absorption column cause relatively large amounts of methane to be absorbed, thereby making the separation of ethane and propane from methane quite difficult and expensive. Due to the market demand for lighter hydrocarbons and the lack of selectivity of lean oils for such components, the absorption process has been gradually replaced by improved processes known as the refrigerated oil absorption, simple refrigeration, cascaded refrigeration, Joule-Thompson, and cryogenic expander processes. The extractive flashing embodiment of the Mehra Process, as disclosed in U.S. Pat. Nos. 4,421,535, 4,511,381, and 4,526,594, utilizes preferential physical solvents for extracting selected amounts of $C_2$–$C_4$ hydrocarbons and all $C_5+$ hydrocarbons from a natural gas by using the steps of flashing, recycling of $C_1$-rich flashed gases, and compression, cooling, and condensing of $C_1$-lean flashed gases, followed by demethanizing the condensate to produce a natural gas liquid (NGL) product and an overhead gas stream which is recycled to the extraction step. Typical recoveries for these processes are compared in Table I.

TABLE I

| COMPARISON OF TYPICAL LIQUID RECOVERIES | | | | |
|---|---|---|---|---|
| EXTRACTION | ETH-ANE (%) | PRO-PANE (%) | BU-TANES (%) | GAS-OLINE (%) |
| ABSORPTION | 5 | 25 | 75 | 87 |
| REFRIGERATED ABSORPTION | 15 | 75 | 90 | 95 |
| SIMPLE REFRIGERATION | 25 | 55 | 93 | 97 |
| CASCADED REFRIGERATION | 70 | 85 | 95 | 100 |
| JOULE-THOMPSON EXPANSION | 70 | 90 | 97 | 100 |
| TURBO-EXPANDER | 85 | 97 | 100 | 100 |
| MEHRA PROCESS | 2–90 | 2–99 | 2–100 | 2–100 |

In summary, the oil absorption, refrigerated oil absorption, simple refrigeration, and cascaded refrigeration processes operate at the pipeline pressures, generally without letting down the gas pressure, but the recovery of desirable liquids (ethane plus heavier components) is poor, with the exception of the cascaded refrigeration process which has extremely high operating costs but achieves good ethane and propane recoveries. The Joule-Thompson and the cryogenic turboexpander processes achieve high ethane recoveries by letting down the pressure of the entire inlet gas, which is primarily (methane (typically 80-85%), but recompression of most of the inlet gas is quite expensive.

As the demand for $C_2$-$C_4$ hydrocarbons has increased over the years, the oil absorption plants have often been redesigned to include refrigeration, thereby becoming refrigerated absorption plants, because lower temperatures enable the lean oil to absorb larger quantities of gaseous hydrocarbons. The simple refrigeration process, which typically recovers 80% of the propane, also typically requires the recovery of 35% of the ethane. In order to boost propane recovery to the 95+% level, cascaded refrigeration, Joule-Thompson, or cryogenic turbo-expander processes have to be used while simultaneously boosting the ethane recovery to 70+% at a considerably larger capital investment.

Of the total of 814 natural gas plants presently in the United States according to Oil and Gas Journal, Jul. 15, 1985, 6% are simple absorber plants and 25% are refrigerated absorption plants. Absorber plants have a capacity of about 5 billion standard cubic feet of gas per day but treat about 2 billion standard cubic feet of gas per day, and refrigerated lean oil absorber plants have a capacity of about 22 billion standard cubic feet of gas per day but treat slightly over 12 billion standard cubic feet of gas per day.

Many of these plants have also experienced a natural decline in gas availability due to their age. Moreover, the reduced volumes and inefficient recoveries for lighter hydrocarbons, such as ethane and propane, have adversely affected their economics. The availability of propane within the United States from all sources falls short of propane demand, thereby requiring propane to be imported in the reported quantities of 66,000 barrels per day in 1985. Consequently, there is a need to improve the economics of such plants by increasing the recovery of $C_2$-$C_4$ hydrocarbons that are present in the locally available gas streams.

At many locations, outmoded lean oil plants have been abandoned and are idle and rusting or are being replaced with new turbo-expander plants being built alongside them at substantial capital expenditures. Such lean oil absorber plants are tremendously varied in their processes; yet they have basic similarities, and each has the same basic need for recovering additional quantities of $C_3$+hydrocarbons and particularly of propane itself in order to retain profitability and avoid abandonment and/or replacement with a more modern plant. There is accordingly a need for a process that can rejuvenate such old plants, without requiring large investments for modernization thereof, by recovery of economically large amounts of $C_3$+ hydrocarbons and particularly of propane itself from the same flow of incoming natural gas. There is further a need to recover economically worthwhile quantities of ethane at some locations.

These lean oil absorber plants generally utilize steps of absorption, distillation and/or flashing for the purpose of excluding undesirable components. These steps are generally followed by regeneration of the absorption oil and recycling it to the absorption step. Then the hydrocarbons are separated from the absorption oil. Nevertheless, as varied as these plants are, their basic steps and apparatuses can be utilized.

Most of the lean oil plants were built during 1940-1960 when the demand for propane and ethane as petrochemical feedstocks was relatively slack, so that the installed equipment is presently not capable of high recoveries of these hydrocarbons. Theoretically, if there were no equipment size limitations, any lean oil absorption plant could recover hydrocarbon components by simply increasing the flowrate of lean oil. But plant design imposes basic limitations; for example, increasing the lean oil flow rate could flood an absorption column and, immediately before flooding, cause the downstream equipment to handle laroe quantities of methane, since lean oils are not selective, and the absorption of components occurs in proportion to their partial pressure. Moreover, practical economics in the market place does not permit equipment to be replaced to eliminate bottlenecks. Therefore, there is a need to improve the hydrocarbon component recoveries without abandoning the existing equipment or resorting to such expensive alternatives as installing the necessary equipment associated with the other processes of cascade refrigeration, Joule Thompson, or Cryogenic turbo expander processes.

It is also important to note that when these plants were originally built, the objective was to make the gas transportable by removing most of the butanes and the gasoline components of the natural gas stream. Thus, the emphasis then was to size the equipment so that it would substantially recover $C_4$'s and heavier components. However, along with such recoveries of $C_4$+, some propane was also recovered because the lean oils were not selective.

In lean oil absorber plants which conventionally deliver residue gas to pipelines at 300-1300 psig, the inlet gas, which is in most cases at about 5 to 150 psig, is compressed in multiple stages to the operating pressure of the absorber. In most plants, the operating pressure of the absorber is selected by the residue gas delivery pressure in order to take advantage of the higher partial pressures for the absorption processes.

It is another characteristic of lean oil absorber plants that most of the lean oils are physical solvents, but they are not preferential physical solvents according to the definition thereof in the parent applications for the Mehra Process. An interesting phenomenon associated with a preferential physical solvent, as defined by relative volatility and loading factor or by preference factor, is that the relative volatility or selectivity of each hydrocarbon being absorbed into the solvent tends to change in response to the characteristics of the solvent. The relative volatility of $C_1$ over $C_2$ in the presence of most lean oils is essentially the same as if the lean oil were absent, i.e. if the selectivity were slightly less than 5.0. There would accordingly be a potential benefit if a preferential physical solvent could be substituted for lean oil in the absorber plants used for processing natural gas where there might be a possibility of changing the absorption behavior in the absorber column and thereby improving the economics.

The lean oils as used in the existing lean oil absorbers are essentially paraffinic base and form an essentially homogeneous mixture of paraffinic hydrocarbons which are of substantially higher molecular weight than the normal hydrocarbons present in a natural gas stream. Therefore they do not show any tendency to change the selectivity characteristics of the hydrocarbon components of the natural gases being treated.

U.S. Pat. No. 2,290,957 describes a process for recovering volatile hydrocarbons, such as propane, butane, and a natural gasoline, from gases containing these components by using two absorption media, one absorbent being lighter or more volatile than the other and being used to contact the gas in the first absorber and the heavier absorbent being used in a second absorber to contact the gas from the light absorbent. The light absorbent is made up of a relatively pure fraction lighter than the finished gasoline. In the first absorber, the light absorbent contains none or at least very little of any constituent lighter than pentane. In the second absorber, the gas is contacted with a heavy absorbent such as mineral seal oil which picks up the light absorbent coming over in the gas from the first absorber. The gas leaving the second absorber is composed of methane and ethane, with only traces of heavier components, and leaves as residue gas.

U.S. Pat. No. 2,321,666 relates to an absorption refrigeration process in which the scrubbing temperatures are as low as about $-100°$ C. and the scrubbing pressures are less than the critical pressure of methane (672 psia). A $C_3$-hydrocarbon liquid is the preferred scrubbing liquid when a $C_2$-hydrocarbon component is to be separated from methane in a normally gaseous mixture.

U.S. Pat. No. 2,620,895 describes a process in which selected heavy constituents are separated from a mixture of natural gases by chilling an aqueous solution of 40% diethylene glycol which dehydrates and chills the gas mixture. A cold lean oil then scrubs the cold, dry gas mixture to remove its heavy constituents. The rich oil is sent to a rectifier or distillation column and then to a chiller.

U.S. Pat. No. 3,236,029 describes a process for separation and recovery of condensable hydrocarbons from natural gas by feeding a lean absorption oil, such as a mineral seal oil, to the upper portion of an absorption column. The overhead stream is residue gas. Rich absorption oil is removed from the bottom of the column and flashed to remove methane. The flashed oil is heated and passed through the upper portion of the stripping section of a de-ethanizing absorber, the bottom portion of which is a stripper having a reboiler.

The extractive flashing embodiment of the Mehra Process, as disclosed in U.S. Pat. Nos. 4,421,535, 4,511,381, and 4,526,594, which are incorporated herein by reference, utilizes preferential physical solvents for the purpose of recovering natural gas liquids from natural gas streams by extracting the natural gas streams with a preferential physical solvent, flashing the rich solvent, and compressing, cooling, and condensing at least one $C_1$-lean vapor fraction which is then demethanized to produce the gas liquids. This embodiment of the Mehra Process thus combines the advantages of the higher-pressure absorption processes by selectively extracting and letting down the pressure of essentially the desired components, thereby reducing the compression of undesired components, such as methane, while achieving high levels of component recovery in a flexible manner. The Mehra Process is capable of overcoming the disadvantages of non-selectivity of common lean oils for lighter hydrocarbons, such as ethane and propane.

The minimum qualifications for the preferential physical solvent utilized in the extractive flashing embodiment of the Mehra Process has a minimum relative volatility of methane over ethane of 5.0 (thereby defining its improved selectivity toward ethane over methane) and a minimum solubility of 0.25 standard cubic foot per gallon (SCF/gal) of the solvent (thereby defining its hydrocarbon loading capacity). Dimethyl ether of polyethylene glycol, having respective values of 6.4 and 1.0, is identified as the preferred preferential physical solvent.

Therefore, it is the combination of improved selectivity towards ethane and the hydrocarbon loading capacity of dimethyl ether of polyethylene glycol that makes it a superior solvent for selectively extracting and recovering the components of a natural gas stream that are heavier than methane. This combination also enables solvent flow rate variations and flashing-pressure variations to be particularly useful for flexibly producing liquid products having selected hydrocarbon compositions. A mixture of dimethyl ethers of polyethylene glycol, having a molecular weight of 146 to 476 and containing 3–10 ethylene units, for example, is a highly satisfactory solvent.

While such solvents are satisfactory for the extractive flashing embodiment of the Mehra Process, they are subject to possible further polymerization and/or thermal degradation if cyclically flowing through a unit operation requiring heating, such as distillation, at the process temperatures used for separation of mixtures into useful fractions or components within equipment used in existing lean oil absorption facilities. There is, therefore, a need for other solvents that are not subject to these limitations.

U.S. Pat. No. 2,846,443 teaches the addition of small quantities of organic compounds, only slightly soluble in water and comprising aromatic hydrocarbons which assist in flocculation of the colloidal suspensions of the polymers derived from acetylene, to special selective solvents, miscible in water, such as dimethylformamide, gamma-butyrolactone, and N-methylpyrrolidone. These aromatic hydrocarbons include toluene, benzene, and homologues of benzene and chlorinated hydrocarbons such as trichloroethylene.

U.S. Pat. No. 3,280,206 relates to liquid-liquid extraction with inert organic solvents such as carbon tetrachloride, chloroform, tetrahydrofuran, diethylene glycol dimethylether, and benzenoid hydrocarbons which are free of olefinic and acetylenic unsaturation and boil at a temperature which is below the boiling point of the high boiler, such as benzene, toluene, ethylbenzene, xylenes, mesitylene, biphenyl, the lower alkyl biphenyls, and the terphenyls, in order to remove high boiling polyphenyls which have been formed by exposure to heat and/or ionizing radiation of organic coolants and coolant-moderators in nuclear reactors.

U.S. Pat. No. 3,349,145 teaches an improvement in a process for the catalytic hydrodealkylation of an alkyl aromatic hydrocarbon feed in the presence of an excess of hydrogen. The process comprises withdrawing from a source of impure hydrogen a hydrogen-rich gas comprising $C_1$–$C_5$ paraffins and countercurrently scrubbing the gas, which is under a pressure of 200–1000 p.s.i.g. and at a temperature below 200° F., with a liquid absorbent consisting essentially of a mixture of $C_9+$ aromatic hydrocarbons, thereby absorbing a substantial portion of the paraffins in the absorbent. The aromatic hydrocarbons utilized as the liquid absorbent may comprise, either in pure form or in admixture with other aromatics, xylenes and higher polyalkyl benzees such as trimethylbenzenes and tetramethylbenzenes. However, alkyl subsituted mononuclear aromatics having more than 3 methyl groups per nucleus or having an alkyl group containing more than 3 carbon atoms are less preferred because of their higher hydrogen equivalency. When the crude hydrogen contains $C_6$, $C_7$, or $C_8$ paraffins, a preferred absorbent comprises a $C_9+$ aromatic hydrocarbon, either in pure form or admixed with other $C_9+$ aromatics, such as propylbenzene, isopropylbenzene, pseudocumene, and mesitylene.

Preferential physical solvents are used in an extractive stripping embodiment of the Mehra Process, as disclosed in Ser. No. 784,566 and Ser. No. 808,463. These solvents are rich in $C_8$–$C_{10}$ aromatic compounds having methyl, ethyl, or propyl alphatic groups and selective for ethane and heavier hydrocarbon components of the gas stream such that: (a) the relative volatility of methane over ethane is at least 5.0 and the hydrocarbon loading capacity, defined as solubility of ethane in solvent, is at least 0.25 standard cubic feet of ethane per gallon cf solvent, or (b) the preferential factor, determind by the multiplication of relative volatility of methane over thane by the solubility of ethane in solvent, in SCF of ethane per gallon of solvent, is at least 1.25.

Many lean oil absorption plant utilize stripping, such as with a reboiler, for removing absorbed hydrocarbons from the rich oil. An example is taught in U.S. Pat. No. 2,516,507 which discloses process for absorbing $C_1$–$C_3$ hydrocarbons from a gaseous mixture thereof that is fed to the midsection of an absorption column which also receives a stream of absorption oil (a mixture of $C_5$–$C_7$ hydrocarbons) at its top. The residue gas is methane. A portion of the $C_1$–+$C_3$ gases are withdrawn as a sidestream, but all of the $C_3$ hydrocarbons is absorbed in the oil below the withdrawal line within the primary absorption zone, wherein the oil is heated by a reboiler to drive off the absorbed $C_2$ hydrocarbons.

U.S. Pat. No. 2,868,326 discloses a process which comprises absorption of a natural gas with absorption oil in a column having a reboiler. Its bottoms are fed to the midsection of a distillation column functioning as a depropanizer. Its overhead condensate is partially refluxed and partially fed to the midsection of a second distillation column functioning as a de-ethanizer.

U.S. Pat. No. 2,938,865 shows a de-ethanizing absorber column having an absorption zone in its upper part, a stripping zone in its lower part, an external reboiler at its bottom, a feed line for absorption oil into the upper portion of the column, and a feed line for a compressed, wet gas into its intermediate portion, between the stripping and absorption zones.

An additional problem that arises in processes using solvents is caued by the presence of small amounts of cyclic hydrocarbons in the gas stream when the cyclic compounds have a higher boiling point (i.e., a higher molecular weight) than the solvent. Under such circumstances, the cyclic compounds tend to build up in the solvent and cause the solvent to lose its preferential characteristics. There is accordingly also a need to provide a process that can maintain the preferential nature of the solvent without interfering with the extraction process

SUMMARY OF THE INVENTION

It is an object of this invention to provide a process to improve the recoveries of desirable components without making any changes to existing equipment in a lean oil absorber plant.

It is another object of this invention to provide a process for recovering up to 100% of propane in a gas absorber plant without having to make substantial changes in its apparatus and/or piping.

It is also an object to provide a process for selectively recovering 2–95% of the ethane in a gas absorber plant without having to make substantial changes in its apparatus and or piping.

It is further an object to provide a process for recovering up to 100% of the propane and as little as 2% of the ethane and methane from a natural gas stream in an existing gas absorber plant without having to make substantial changes in its apparatus and/or piping.

It is additionally an object to provide a new and useful process for economically recovering aliphatic hydrocarbons from a natural gas stream without substantially changing the existinq equipment or arrangement thereof.

It is still further an object to provide a process for using a monocyclic aromatic solvent having $C_8$–$C_{10}$ hydrocarbons as a preferential physical solvent.

In accordance with these objectives and the principles of this invention, a process is herein provided which comprises the utilization of a preferential physical solvent in an existing absorber plant, an existing refrigeration absorption plant, or an existing extractive stripping plant. This solvent has a relative volatility of methane over ethane at least 6.0 and an ethane solubility of at least 1.0 SCF/gal, a preferential factor of at lest 6.0 and is useful in replacing the absorber lean oil, for which the plant was designed, thereby producing ethane and propane in hitherto unavailable quantities. It has also been discovered that, by restricting the preferential physical solvent to these higher values of relative volatility, solubility, and preferential factor than those disclosed earlier in Mehra applications, the effective selectivity of the preferential physical solvent for this invention is thereby defined.

It has been found that it is surprisingly feasible to recover additional $C_2$ and $C_3$ hydrocarbon products without significantly modifying the existing equipment because the selectivity of such preferential physical solvent permits such recoveries without simultaneously requiring processing of substantial amounts of undesirable components such as methane or ethane, depending upon the desired objectives of the recovery process.

It is important to note the difference between the processes of absorption and extraction. In "Mass Transfer Operations" by Robert E. Treybal, McGraw Hill Book Company, Second Edition, 1968, pages 220–226, absorption has been defined as an operation in which a gas mixture is contacted with a liquid for the purposes of preferentially dissolving one or more components of the gas and providing a solution of one or more of these components in the liquid. The solubility of a gas in an absorption medium is of primary importance. Since butanes and pentanes form an ideal solution with higher molecular weight paraffin oils, the solubility of the gas is the same in terms of mole fractions for all solvents. These systems follow Raoult's and Henry's laws which define solubility as a function of partial pressures.

On page 395 of the above reference, Treybal defines the primary requirement of a satisfactory extractive distillation solvent as being its ability to be highly selective or possess the ability to alter the vapor-liquid equilibrium of the original mixture sufficiently to permit its easy separation, with, however, use of only small quantities of the solvent being desired.

In addition, John H. Perry in "Chemical Engineers' Handbook" Fourth Edition, McGraw-Hill Book Company, pages 13–46 and 13–47, defines extractive distillation as the addition of a separating agent, solvent, to the column to alter favorably the relative volatilities of the feed components. However, the solvent must usually be added in fairly large amounts so that column diameters and heat loads are increased, and plate efficiencies may be lowered. It is further defined that the most important characteristics of the solvent are its selectivity and capacity. Selectivity is defined as the relative volatility of the feed components in the presence of the agent divided by the relative volatility of the feed components in the absence of the agent. The capacity of the solvent is defined as the liquid concentration of the feed components in the solvent in which the selectivity is measured.

In absorption, only solubility plays a role. In extraction, both solubility and selectivity play important roles. Solubility implies molecules entering the solvent surface, but selectivity involves molecules escaping from the solvent surface. Solubility is proportional to partial pressure, as stated by Henry's Law. Selectivity defines the relative volatility of one hydrocarbon, for example, to another hydrocarbon with respect to the same solvent, as $C_2$ to $C_1$ or $C_3$ to $C_1$ or $C_3$ to $C_2$.

The absorption principle leads to an alpha or relative volatility for methane with respect to ethane of slightly less than 5 for almost all known absorption liquids. However, the relative volatility for methane with respect to ethane in the presence of dimethyl ether or polyethylene glycol (DMPEG) is 6.4, indicating that it is more selective toward ethane than many other absorption liquids.

The effect of substituting a preferential physical solvent for a lean oil in an existing plant is to "spread apart" the selectivities of the extracted hydrocarbons. Such "spreading" is indicated in the following table for ethane and propane with respect to methane, using the R values in "High $CO_2$-High $H_2S$ Removal with SELEXOL SOLVENT", by John R. Sweny:

| Solvents | α Values | | α Spread Between |
| --- | --- | --- | --- |
|  | $C_3$ | $C_2$ | $C_3$ and $C_2$ |
| Lean Oil | 12.5–13.0 | 5.0 | 7.5–8.0 |
| DMPEG | 15.3 | 6.4 | 8.9 |

The advantage imparted by such spreading apart of λ values by a preferential physical solvent is that the selected solutes can be separated more easily (e.g., $C_1$ from $C_2+$ hydrocarbons) within the column-confined descending solvent droplets and ascending gases as equilibrium is reached by each hydrocarbon solute.

N-methyl pyrrolidone (NMP) and dimethyl formamide (DMF) have relative volatilities for methane/ethane of 5.3 and 8.5, respectively. However, the solubility of hydrocarbons in NMP is 0.03 standard cubic feet per gallon (SCF/GAL) and in DMF is 0.04 SCF/GAL; these values are low when compared to 1.0 SCF/GAL for DMPEG. Similarly, the relative volatility of methane over ethane in the presence of mesitylene is 6.9, thereby indicating it to be even better than DMPEG, while simultaneously it possesses a solubility of 4.2 SCF/gal of ethane, thereby indicating its much greater loading capacity. Clearly, mesitylene is better than DMPEG, since its preferential factor is 29 when compared to that of DMPEG of 6.4, and substantially superior to lean oils having a preferential factor of 0.96.

The preferential physical solvent may be dialkyl ethers of polyalkylene glycols, alkyl substituted monocyclic aromatic $C_8$–$C_{10}$ hydrocarbons, mixtures of these hydrocarbons, or such mixtures as a reformate stream or a recovered stream from a refinery cracking process.

Suitable preferential physical solvents more specifically include aromatic streams in petroleum refineries and petrochemical plants that are rich in monocyclic $C_8$–$C_{10}$ aromatic compounds having methyl, ethyl, or propyl aliphatic groups, including mesitylene, n-propyl benzene, n-butyl benzene, o-xylene, m-xylene, p-xylene, and mixtures thereof, rich being defined as more than 15% by weight. These compounds boil in the range of 270°–425° F.

Suitable sources of these $C_8$–$C_{10}$ aromatic compounds are aromatic streams, such as in petroleum refineries that are rich in mixed xylenes, $C_9$ alkylaromatics, and other $C_8$–$C_{10}$ aromatics. These compounds boil in the range of 270°–425° F. and are stable at the process temperatures used in separating mixtures into useful fractions and/or components, such as in distillation, extractive stripping, and extractive distillation operations. Moreover, they are also hydrocarbons which can be left in the liquid products in trace amounts, without interfering with use of such products in gasoline, for example, so that purification of the liquid products is not needed.

A principal refinery source of $C_8$–$C_{10}$ aromatic feed streams may be found in catalytically reformed naphthas in which a $C_9$ heart cut or extract of the reformate is enriched in $C_9$ alkylbenzenes, a typical reformate containing as much as 57% trimethylbenzenes based on the total content of $C_9$ aromatics. The composition of a $C_9$ heart cut is typically about 2.5, 87.5 and 10 mole % of $C_8$, $C_9$ and $C_{10}$ aromatics, respectively. Other sources of $C_8$–$C_{10}$ aromatic feedstocks are derived from gasoline producing processes such as the conversion of methanol to gasoline, as described in U.S. Pat. Nos. 3,931,349, 3,969,426, 3,899,544, 3,894,104, 3,904,916 and 3,894,102, and the conversion of synthesis gas to gasoline as described in U.S. Pat. Nos. 4,096,163, 4,279,830, 4,304,871 and 3,254,023, all of which are incorporated by reference. A $C_7$–$C_9$ mixed aromatic feedstock also may be used and can be derived from various sources including petroleum refinery sources, pyrolysis of coal to produce coke, tar sands, etc.

In petroleum processing operations such as transalkylation, isomerization, and disproportionation, for example, the product streams so produced are further treated, by fractionation and the like, to obtain alkylaromatic streams which contain substantial quantities of alkylbenzenes such as toluene, xylenes, and trimethylbenzenes. A typical alkylaromatic fraction which may be obtained contains predominantly $C_7$ to $C_9$ hydrocarbons and is referred to as crude xylenes.

Refinery streams suitable as preferential physical solvents for the present process are $C_9$ alkylaromatics, a $C_7$ to $C_9$ mixture of alkylaromatics, or a $C_8$–$C_{10}$ mixture of alkylaromatics. The $C_9$ alkylaromatic hydrocarbons are characterized as mainly monocyclic aromatic compounds, such as alkylbenzenes, which have at least one alkyl group which preferably contains no more than 4 carbon atoms. The $C_9$ aromatic hydrocarbons include, for example, 1,2,3-trimethylbenzene (hemimellitene), 1,2,4-trimethylbenzene (pseudocumene), 1,3,5-trimethylbenzene mesitylene), isopropylbenzene (cumene), 1,2-methylethylbenzene, 1,3-methylethylbenzene, and 1,4-methylethylbenzene.

The $C_9$ alkylaromatics for use in the present process are conveniently available as product streams from various petroleum processing operations, including gasoline producing processes such as the conversion of methanol to gasoline or the conversion of carbon monoxide and hydrogen (syngas) to gasoline. Catalytic reformates, for example, are particularly preferred since they are enriched in aromatics and the C$_9$ fraction can be readily separated from non-aromatics by extraction with aqueous glycols, typically a Udex unit. The typical composition of extracted C$_9$ reformate and the boiling points of the C$_9$ aromatics contained therein are shown below in Table II.

TABLE II
COMPOSITION OF C$_9$ AROMATICS IN EXTRACTED REFORMATE

| Compound | Boiling Point (°F.) | Freezing Point (°F.) | Wt. % (based on total C$_9$ aromatics) |
|---|---|---|---|
| Isopropylbenzene | 306 | −141 | 0.6 |
| n-Propylbenzene | 319 | −147 | 5.2 |
| m-Ethyltoluene | 322 | −140 | 17.4 |
| p-Ethyltoluene | 324 | −80 | 8.6 |
| 1,3,5-Trimethylbenzene (mesitylene) | 329 | −49 | 7.6 |
| o-Ethyltoluene | 329 | −114 | 9.1 |
| 1,2,3-Trimethylbenzene (pseudocumene) | 337 | −47 | 41.3 |
| 1,2,3-Trimethylbenzene (hemimellitene) | 349 | −14 | 8.2 |
| Indane | 352 | — | 2.0 |
| | | | 100.0% |

While the quality of crudes may affect the quantity and type of C$_9$ aromatics extracted from a naphtha reformate, about 57 wt.% of the total C$_9$ aromatics are trimethylbenzenes in which pseudocumene, mesitylene, and hemimellitene are typically produced in the following ratios:

Pseudocumene = 1
Mesitylene = 0.18
Hemimellitene = 0.20

The C$_9$ aromatics may be further characterized as having an initial boiling point range of 230°–280° F., an end boiling point range of 350°–425° F., and an API gravity of 35–60.

A useful, although not ideal, source of preferential physical solvent is primarily a mixture of seven to nine carbon atom alkyl aromatics which include C$_7$ and C$_8$ aromatics, such as toluene, ethylbenzene and xylenes, and C$_9$ alkyl-aromatics identified in Table II above. Such charge stocks may also be derived from catalytic reformates, pyrolysis gasoline, etc., by distillation and solvent extraction to separate aromatic compounds from aliphatics. Other sources of suitable charge stocks include crude xylene streams, which actually contain alkylaromatics having 7 to 9 carbon atoms, and effluents from toluene transalkylation reaction zones which contain benzene, xylene, C$_9$ aromatics, and aromatics heavier than C$_9$. Mixtures of toluene and C$_9$ alkylaromatics may also be employed. The composition of a typical C$_7$–C$_9$ reformate cut is shown below in Table III.

TABLE III

| Products: | Analysis wt. percent |
|---|---|
| Naphthenes | 0.15 |
| Benzene | 2.03 |
| Toluene | 19.69 |
| Ethylbenzene | 0.004 |
| Paraxylene | 12.04 |

TABLE III-continued

| Products: | Analysis wt. percent |
|---|---|
| Metaxylene | 27.64 |
| Orthoxylene | 10.40 |
| p-Ethyltoluene | 0.02 |
| m-Ethyltoluene | 0.06 |
| o-Ethyltoluene | 0.01 |
| Mesitylene | 7.18 |
| Pseudocumene | 15.82 |
| Hemimellitene | 1.93 |
| Ethylxylenes | 0.13 |
| Durene | 1.19 |
| Isodurene | 1.43 |
| Prehnitene | 0.28 |

The C$_7$ to C$_9$ aromatic mixture may be further characterized as having an initial boiling point range of 150° F., an end boiling point range of 350° F., and an API gravity of about 40.

Returning to the description of this process, the preferential physical solvent is fed to the top of an existing absorber, which operates as an extractor for the process of this invention, or to the top of an extractive stripping column. The inlet feed gas stream is fed through the bottom of the same extractor or into the midsection of the extractive stripping column. This gas is generally natural gas.

The preferential physical solvents are defined for the purposes of this invention as having a minimum relative volatility of methane over ethane of at least 6.0 (thereby defining their improved selectivities toward ethane over methane) and in addition a solubility of at least 1.0 standard cubic foot of gaseous hydrocarbons per gallon of the solvent (SCF/GAL) (thereby defining their hydrocarbon loading capacities), or, alternatively, a preferential factor of at least 6.0. The preferential factor for physical solvent selection in the Mehra Process is defined as a product of relative volatility of methane over ethane multiplied by the solubility of hydrocarbons in physical solvents, specified as standard cubic feet of ethane per gallon (SCF/gal). However, the ideal preferential physical solvent would have a selectivity toward ethane over methane of at least 10.0 and would simultaneously possess a hydrocarbon loading capacity of at least 3.0 SCF/GAL.

This combination of minimum relative volatility and minimum solubility enables solvent flow rates and operating pressures to be selectively utilized in a wide variety of existing simple absorber and refrigerated absorber plants, including those having either flashing or stripping equipment for separating extracted hydrocarbons from the solvent. These rejuvenated plants not only produce propane in hitherto unavailable quantities but are also capable of producing liquid or gas products having selected hydrocarbon compositions.

Preferential factors are given in the following Table IV for N-methyl pyrollidone (NMP), dimethyl formamide (DMF), a common lean oil, the minimum solvent having desired requirements for the process of this invention, DMPEG, mesitylene, and the ideal solvent. These preferential factors are important because they inversely indicate the amount of solvent which is required, in terms of solvent flow rate, for a given recovery level of desirable hydrocarbons. In other words, as 6.4 is much greater than 0.16, the amount of NMP required would be approximately 40 times the amount of DMPEG required for the same performance, if NMP were used for the process of this invention.

TABLE IV

Preferential Factors Defining Preferential Physical Solvents for Mehra Process Applications

| SOLVENT | NMP | DMF | LEAN OIL | MIN. | DMPEG | MESIT-YLENE | MIN. FOR IDEAL |
|---|---|---|---|---|---|---|---|
| Relative volatility ($\alpha$) | 5.3 | 8.5 | 2.5–4.8 | 6.0 | 6.4 | 6.9 | 10.0 |
| Solubility, SCF/gal., $\gamma$ | 0.03 | 0.04 | 0.2–1.0 | 1.00 | 1.0 | 4.2 | 3.0 |
| Preferential factor ($\alpha \times \gamma$) | 0.16 | 0.34 | 0.5–4.8 | 6.00 | 6.4 | 29.0 | 30.0 |

The process of this invention uses a preferential physical solvent for extracting propane and heavier hydrocarbon components from a natural gas stream, such as a natural gas stream, at maximum $C_{3}+$ recovery while recovering as little as 2% of $C_2$ and $C_1$ hydrocarbons. By substituting a preferential physical solvent in lieu of absorber oil in an existing lean oil plant, the process of this invention can achieve a propane recovery that is surprisingly better than prior art recoveries from the same equipment arrangement. In addition, the recovery level from this invention varies according to the specific solvent which is chosen for the process according to the solvent which is chosen and the relative partial pressures of desirable components in the natural gas stream.

The process of this invention thereby produces a gas or liquid hydrocarbon product from an existing absorption plant or from an existing refrigerated absorption plant which has a composition that is selective depending upon the plant economics, is exceptionally superior, with respect to minimum content of methane or methane, and ethane, and unusually valuable, because of enhanced economically desirable component such as ethane or component, as compared to products obtained with prior art absorber lean oil when utilized in the same equipment.

If the lean oil plant is of the absorption type, the recovery of propane can be significantly increased by using alkyl substituted monocyclic aromatic $C_8$–$C_{10}$ hydrocarbons as the solvent. Mesitylene, for example, gives excellent results, and a mixture of alkyl substituted monocyclic aromatic $C_8$ hydrocarbons improves propane recovery even more, without any noteworthy change in piping or other equipment. However, propane yields can be further increased by recycling of streams of $C_1$-rich gases to the existing absorber, operating as an extractor with preferential solvents or mixtures thereof if such $C_1$-rich streams are available, as taught in U.S. Pat. Nos. 4,421,535, 4,511,381, and 4,526,594. Other equipment changes that are known in the art can also be made and are likely to be economically worthwhile because the preferential physical solvent used in the process of this invention is a powerful tool that responds to available opportunities.

If the lean oil plant is of the extractive distillation or extractive stripping type, propane recoveries are even higher, for each respective solvent, than the propane recoveries in the absorption plant. Extractive distillation or stripping of the feed gas, as is known in the art, can be followed by a wide variety of distillation or stripping columns for solvent regeneration, product recovery, and the like. These units can affect yields of $C_{3}+$ hydrocarbon recovery, but in any such plant, it is generally true that the use of a preferential physical solvent, within the selectivity and volatility or preference factor limits of the invention, gives surprisingly better results than lean oil performance.

The use of a preferential physical solvent in an existing absorber plant, so that the plant operates in extraction mode, causes the $C_{2}+$ hydrocarbon components to change their relative volatility relationships to each other as clearly as to methane. The attraction of ethane, for example, toward the preferential physical solvent is relatively so much greater than toward a lean oil that it may be thought of as tending to "crowd out" or displace the methane as the ethane becomes fully absorbed (i.e., to the capacity of the solvent) at the proper balance of gas and solvent flow rates.

However, at the same gas flow rate and at a lesser solvent flow rate, the propane may be thought of as tending to displace both the methane and the ethane as it becomes fully absorbed by the preferential physical solvent. Because of the change in absorptive behavior, an absorption operation becomes an extraction operation in the process of this invention.

In an absorption process for the removal of $C_{2}+$ hydrocarbons from a natural gas stream by absorbing the $C_{2}+$ hydrocarbons with a lean oil to produce a residue gas stream of pipeline quality and a rich solvent from which the $C_{2}+$ hydrocarbons are recovered, wherein a need exists for recovering at maximum recoveries for the available equipment a selected hydrocarbon component and heavier hydrocarbons within the group consisting of ethane, propane, butane, and pentane without the need simultaneously to recover hydrocarbons lighter than the selected hydrocarbon component from the natural gas stream, the selected component being ethane, propane, or butane, and for recovering to a selected degree the hydrocarbon lighter than the selected hydrocarbon component when the lighter hydrocarbon is ethane or propane, the improvement of this invention comprises providing the capability, within the available equipment, of selectively extracting $C_{2}+$ hydrocarbons from the gas stream with a lean preferential physical solvent according to the maximum recoveries and to the selected degree of (a) ethane in amounts ranging up to 70%, (b) propane in amounts ranging up to 95%, (c) butane in amounts ranging up to 98%, or (d) pentanes and higher molecular weight hydrocarbons in amounts ranging up to 99% by:

A. selecting an absorber plant, having the available equipment, which is used for recovering maximum quantities of the $C_{2}+$ hydrocarbons from the gas stream while using lean oils as solvent for the $C_{2}+$ hydrocarbons;

B. selecting a preferential physical solvent which is selective for ethane and heavier hydrocarbon components of the gas stream such that the relative volatility of methane over ethane is at least 6.0 and the solubility of ethane in the solvent is at least 1.0 standard cubic foot of ethane per gallon of the solvent or the preferential factor is at least 6.0;

C. replacing the lean oils in the selected absorber plant with a selected volume of the selected preferential physical solvent; and D. while using the equipment in extraction mode, contacting the gas stream with the lean preferential physical solvent at a selected flow rate within the range of 0.001–0.5 gallon of lean solvent per standard cubic foot of the gas stream to produce a residue gas stream of pipeline specifications and a rich solvent stream containing the ethane and heavier hydrocarbon components.

The natural gas stream used as feedstock is selected from the group consisting of:

A. natural gas at up to saturation with water:
B. sweet natural gas;
C. dry natural gas; and
D. sour natural gas which is pre-sweetened in gas phase with an aqueous amine solution and dried with an aqueous glycol solution.

The improved process of the invention further comprises:

A. selectively flashing or stripping the rich solvent stream to produce a gas fraction for recycling and a hydrocarbon-containing solvent stream; and B. distilling the hydrocarbon-containing solvent stream to produce a stream of lean preferential physical solvent and a stream of the selected hydrocarbon component and the heavier hydrocarbon components as a product while recovering the lighter hydrocarbons only to the selected degree.

The replacing column may be designed as an extraction column having a reboiler and a stripping section, whereby additional selectivity is provided to the improved process by carrying out the selectively extracting and stripping of the natural gas stream with the preferential physical solvent, thereby gaining an additional degree of freedom.

This additional degree of freedom is effectively utilized by appropriately selecting the reboiling temperature at the bottom of the column in order to produce the rich solvent stream consisting essentially of only economically desirable hydrocarbons out of the ethane and heavier hydrocarbon components, thereby rejecting economically undesirable hydrocarbon components.

A stream of the rejected undesirable hydrocarbon components, flowing upwardly through the stripping section of the column, contains some desirable hydrocarbons which are recovered preferentially by mass transfer principles by transfer to the physical solvent. The rejected hydrocarbons, stripped from the rich solvent, leave the stripping section of the column and join the incoming natural gas stream to form a combined stream which flows upwardly in the extraction section of the column, wherein the lean solvent preferentially recovers any contained desired hydrocarbons. The rich solvent leaving the bottom of the column may be let down in pressure to a pressure level that is consistent with the operation of a distillation column for conducting said distilling of the hydrocarbon-containing solvent.

It sometimes happens that lean oil absorber plants are under-designed with respect to a single piece of equipment or a single unit operation, such as, for example, the absorber column, as compared to the remainder of the equipment. If the plant had not been run at capacity because of a slack market or inadequate gas supplies, the potential bottleneck would not have been noticed or at least would have occasioned no difficulty.

It would therefore make good economic sense to replace the undersized equipment, such as the absorber column, with full-sized equipment. Indeed, the absorber column could appropriately be replaced with an extractive stripper column having a reboiler at its bottom. However, operating the process with a replaced extraction column (without a reboiler) or with an extractive stripping column while using a preferential physical solvent instead of the lean oil and at a flow rate of 0.001–0.5 gallon of lean solvent per standard cubic foot of the inlet gas provides the capability of considerably exceeding past performance of the lean oil plant.

BRIFF DESCRIPTION OF THE DRAWINGS

The invention may be more readily understood by referring to the drawings which diagrammatically illustrate preferred embodiments for treating natural gases for removal of hydrocarbons heavier than methane from an inlet gas stream. In FIGS. 1-3, the arrangement of the apparatus is typically found in conventional lean oil absorption plants.

DESCRIPTION OF THE PREFERRED EMBODIMENTS

Figure 1:
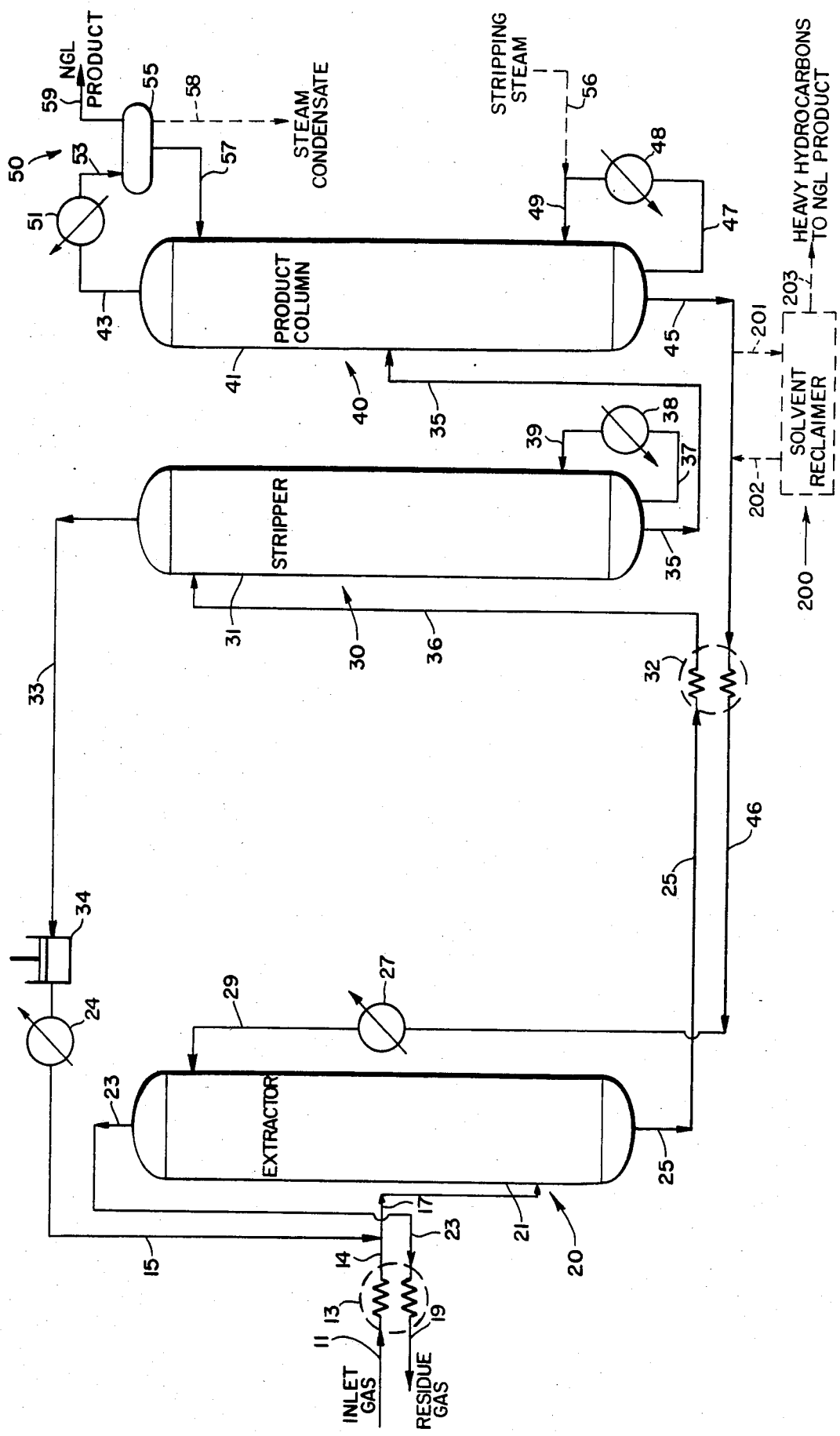
FIG. 1 is a schematic flow sheet for extraction of an inlet gas stream and a recycle gas stream with a preferential physical solvent to produce a liquid product stream and a residue gas stream by using three treating units.

With reference to the drawings, it should be understood that pipelines are in fact being designated when streams are identified hereinafter and that streams are intended, if not stated, when materials are mentioned. Moreover, flow-control valves, temperature-regulatory devices, pumps, and the like are to be understood as installed and operating in conventional relationship to the major items of equipment which are shown in the drawings and discussed hereinafter. The term, "absorber", is employed for an existing gas/solvent facility, but when it is utilized in the process of this invention with a preferential physical solvent, it is considered to be an "extractor".

The process shown schematically in the flow sheet of FIG. 1 comprises an extractor unit 20, a stripper unit 30, and a product unit 40. Inlet gas stream 11 enters an optional heat exchanger 13 and becomes cooled inlet gas stream 14 which combines with recycled gas stream 15 to produce combined gases 17 for use as feedstock to extractor unit 20. Depending upon operating temperatures in the extractor column, cooling is supplied within the optional heat exchanger 13 by overhead stream 23 which becomes heated residue gas stream 19, thereby recovering available cooling energy.

After entering column 21 of extractor unit 20 at pressure which varies between 250-1300 psig, feedstock 17 rises countercurrently to the downward flow of a lean preferential physical solvent stream entering the top of column 21 from line 29 after being cooled in cooler 27. The cooler 27 generally operates such that the temperature of lean solvent in stream 29 is $-20°$ F. or warmer. Overhead stream 23 leaves the top of column 21 for passage to heat exchanger 13. Bottoms in column 21 leave through line 25 to become feedstock for stripper unit 30.

Before entering column 31 of stripper unit 30, bottoms in line 25 passes through optional heat exchanger 32 to become heated bottoms line 36. The pressure in extractor column 21 is at pressure in the order of 250-1300 psig, but the pressure in stripper column 31 may be at lower pressure of the order of 100 to 1300 psig, so that heated bottoms 36 flash when entering column 31. The flashed gases leave the top of column 31 through line 33, are compressed by compressor 34 and cooled by cooler 24, and pass through line 15 to join the inlet gas in line 14 and become combined feedstock in line 17 for column 21 at the inlet gas pressure. Bottoms of column 31 are recycled through line 37 to reboiler 38 and line 39 for supplying heat to the contents of column 31. Since the vapors leaving as line 33 may contain some desirable components such as propane and ethane, the recycling of line 33 to the inlet to the extractor unit 20 results in improved recoveries of the desirable components. Bottoms are discharged through line 35 to product column 41. Optionally the bottoms in line 35 may also be heated before entering the product column 41. Depending upon the relative operating pressure of the product column 41, the bottoms in stream 35 may be pumped if the pressure in the stripper column 31 is lower than the operating pressure of column 41.

At the entrance of column 41, bottoms 35 are further heated by passing through line 47, reboiler 48, and line 49. Overhead leaves through line 43 at the top of column 41, and bottoms leave through line 45 to pass through optional heat exchanger 32 and enter cooler 27 through line 46.

Overhead stream 43 is cooled and condensed in condensing unit 50 and in particular in a partial or total condenser 51 and passes through line 53 to accumulator 55 from which a reflux stream enters column 41 through line 57, and a gas or liquid NGL product stream leaves through line 59.

In summary, the purpose of the extractor unit 20 is to selectively extract desirable components of inlet gas stream 11 by effectively utilizing the selectivity of the preferential physical solvent in stream 29. The purpose of the stripper unit 30 is to reject undesirable components of the inlet gas stream that may be present in the rich solvent streams 25 and 36 and prevent them from leaving with the desirable components present in stream 35 which consists primarily of the desirable components and the preferential physical solvent. The operating pressure of the stripper 31 can be the same as that of the extractor 21, but is generally lower than the operating pressure of extractor 21 in order to affect the separation of undesirable components. The reboiler unit 38 may obtain heat energy either from an external source or as waste heat from the lean solvent in stream 45. The stripper unit 30 may be referred to as a stabilizer, deethanizer, demethanizer, stripper and the like but meaning the same as described above.

The purpose of the product column unit 40 is to separate desirable hydrocarbons from the preferential physical solvent as present in line 35 to produce a lean solvent stream 45 for recycling to the extractor unit 20. The operating conditions of the product column 41 are selected such that the operating temperature at the bottom is no greater than the boiling point of pure solvent. Furthermore, the operating pressure at the top of the product column is selected such that the reflux can be condensed with a conventional cooling source such as ambient air or cooling water. Refluxing column 41 is important in order to minimize losses of the solvent with the hydrocarbon liquid product in stream 59. Depending upon the relative concentration of desirable components in the inlet gas stream 11 and recovery of those components, the condenser 51 may be a partial condenser for generating sufficient reflux or condensing the entire product with a total condenser. The product column 41 may utilize heat from external sources through reboiler 48 or solvent can be stripped by steam injection through line 56 via line 49 and the steam condensate is recovered from the overhead accumulator 55 via line 58.

Figure 2:
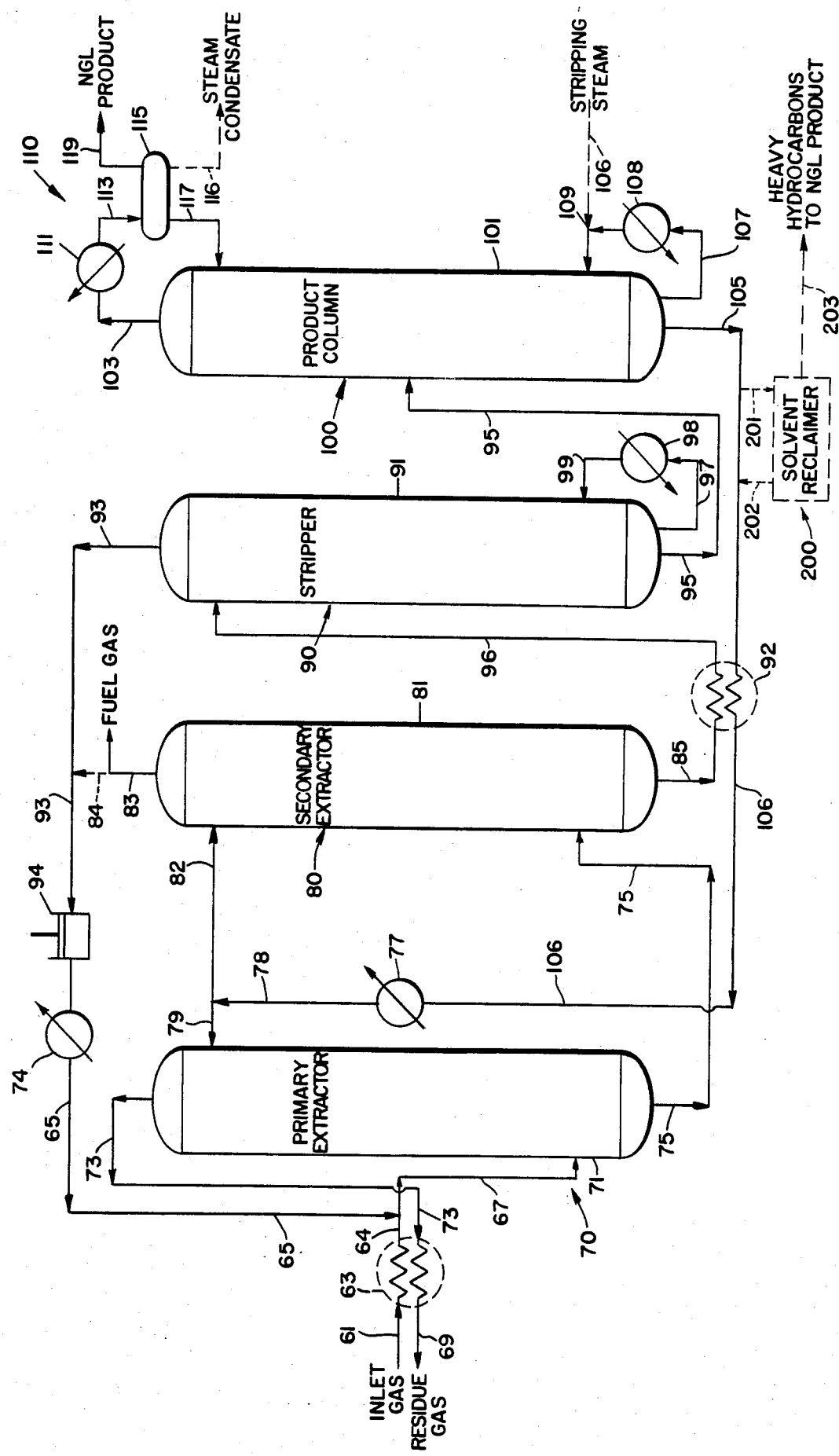
FIG. 2 is a schematic flow sheet for extraction of an inlet gas stream and a recycle stream with a preferential physical solvent by using four treating units to produce a fuel gas stream and a natural gas liquids (NGL) product stream and a residue gas stream having more exact specifications than the corresponding products of the process shown in FIG. 1.

Referring to FIG. 2, inlet gas 61 enters an optional heat exchanger 63 and becomes cooled gas 64 which is joined by an overhead recycle gas stream 65 from compressor 94 and aftercooler 74 to become combined gases 67 as feedstock for primary extractor column 71. Depending upon the operating temperatures of extractor 71, the overhead gas stream 73 also passes through optional heat exchanger 63 to become heated gas stream 69 as residue gas for feeding to a pipeline.

Lean preferential physical solvent, after cooling in cooler 77, passes through line 78, and a major portion flows to the top of primary extractor column 71 through line 79 and thereafter flows downwardly, countercurrently to the gases entering from line 67. Bottoms from column 71 are discharged through line 75 and become feedstock for column 81 of secondary extractor unit 80.

The remaining portion of the lean solvent in line 78 flows through line 82 to the top of column 81, thereafter flowing downwardly and countercurrently to upwardly flowing gases from line 75. Overhead is discharged through line 83 for use as fuel gas. The gases in stream 83 may be recycled to line 93 if so desired via line 84. Bottoms are discharged from column 81 through line 85 to enter optional heat exchanger 92.

The heated solvent from optional heat exchanger 92 flows through line 96 to enter near the top of column 91 of stripper unit 90, as feedstock therefor. Overhead from column 91 leaves through line 93 to enter compressor 94. Bottoms are heated by passage through line 97, reboiler 98, and recycle line 99. Bottoms are discharged through line 95 to become feedstock for column 101 of product unit 100.

Overhead is discharged from the top of column 101 through line 103, and bottoms are discharged through line 105 to pass through optional cooler 92 and line 106 to cooler 77. Bottoms in column 91 are heated by passage through line 107, reboiler 108, and recycle line 109.

Overhead stream 103 is cooled and condensed in partial or total condenser 111 of condenser unit 110, and the condensate passes through line 113 to accumulator 115, wherein liquid is refluxed through line 117 to the top of product column 101. A gas or liquid NGL product is removed from accumulator 115 through line 119.

The purpose of primary extractor unit 70 in FIG. 2 is similar to the function of extractor unit 20 of FIG. 1. However, the secondary extractor unit 80 operates at an intermediate pressure between the operating pressures of the primary extractor 71 and stripper 91. The vapor in the secondary extractor 81 is created by lowering the pressure of the rich solvent stream 75. In reducing the pressure, the contained undesirable components of inlet gas stream 61 are preferentially separated from the physical solvent. Unfortunately, some of the desirable hydrocarbons also vaporize even though most of them stay with the physical solvent that leaves in stream 85. Since the relative partial pressures of the desirable hydrocarbons are substantially higher in the vapors created by flashing in unit 80, it is significantly easy to further improve the recovery of desirable hydrocarbons by subjecting to additional contact with lean physical solvent from stream 82. Thus, the combined solvent from line 82 and line 79 flows out of the secondary extractor 81 through line 85.

The functions of stripper unit 90 and product unit 100 are almost identical to the operating requirements described for units 30 and 40 of FIG. 1. Similar to unit 40 of FIG. 1, stripping steam in line 106 may be effectively utilized, if available, for stripping desirable hydrocarbons from the solvent in order to produce a lean preferential physical solvent in stream 105, whereas the steam condensate is recovered from the system via stream 116.

Figure 3:
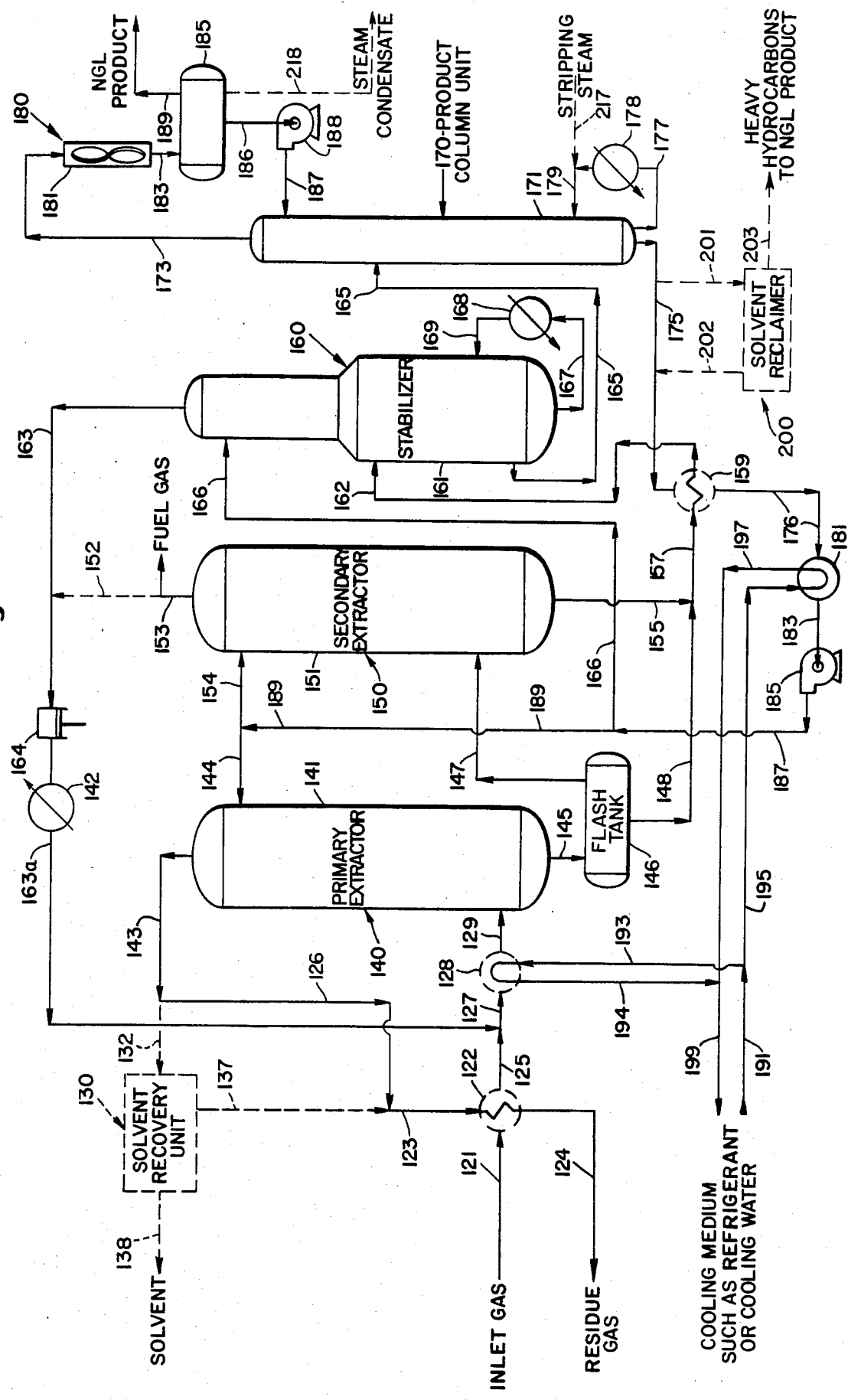
FIG. 3 is a schematic flow sheet for extraction of an inlet natural gas stream and a recycle gas stream by using five treating units, wherein flashing to a lower pressure is used in at least one unit and reboiling is used in at least one unit, to produce a natural gas liquid product and a residue gas product having desired and exacting specifications with maximum thermal efficiency in the process.

Referring to FIG. 3, inlet gas in line 121 passes through an optional cross exchanger 122 to enter line 125 and be joined by a recycle stream in line 163a to become a combined gas stream in line 127. This stream passes through an optional inlet gas chiller 128 and then through line 129, as twice-cooled inlet gas at a temperature of not less than $-20°$ F., to become feedstock for column 141 of primary extractor unit 140.

Overhead from extractor 141 leaves through line 143 and may be subjected to an optional solvent recovery unit 130 by passing through inlet line 132 and outlet line 137 to join line 123 and then to pass through heat exchanger 122 and leave the process through line 124. Recovered solvent leaves unit 130 in line 138. The solvent recovery may consist of a cryogenic unit, molecular sieve or alumina beds, or activated carbon beds for the removal of contained solvent in the residue gas stream 143. The solvent content of stream 143 is a function of molecular weight and vapor pressure of the solvent and the operating conditions of temperature and pressure in the primary extraction column 141. Depending upon the economics of solvent recovery unit 130, the residue stream 143 may by-pass via line 126 to line 123 for heating via optional exchanger 122 to enter residue gas line 124. This solvent recovery unit may be effectively employed on stream 23 of FIG. 1 and stream 73 of FIG. 2 in a similar manner.

It may also be economically preferable to utilize a heavy hydrocarbon oil with molecular weights in the order of 180 to 230 to utilize a small section, above the point where preferential physical solvent enters the primary extraction column, to recover solvent vapor from the residue gas stream in lines 23, 73 and 143. The hydrocarbon oil containing extracted solvent is removed from the primary extractor column and the hydrocarbon never enters the extraction section. The removed hydrocarbon oil can be fractionated to recover solvent overhead for recycle to the preferential physical solvent loop, while the regenerated hydrocarbon oil is recycled back to the solvent recovery section.

The lean preferential physical solvent enters column 141 through line 144 and flows countercurrently to feedstock of stream 129. Bottoms leave column 141 in line 145 and are flashed from a pressure of 250 to 1300 psig to a pressure of 100 to 600 psig in flash tank 146. Flashed gases leave through line 147 to enter column 151 of secondary extractor unit 150 as feedstock therefor. Bottoms leave through line 148.

A lean solvent stream enters the top of column 151 through line 154 and passes downwardly and countercurrently to the upwardly moving stream of gases from line 147 within column 151. The overhead from column 151 leaves through line 153 as fuel gas or may be recycled to stream 163 via line 152. Bottoms from column 151 leave in line 155 and are joined by the solvent stream in line 148 to become a combined stream in line 157 which then passes through an optional cross exchanger 159.

The mixture of solvent and hydrocarbon components in line 162, after passing through cross exchanger 159, is fed to stabilizer column 161 of stabilizer unit 160, at the same time dropping from a pressure of about 100 to 600 psig to a pressure of about 80 to 400 psig within column 161. A portion of cool lean solvent is fed to column 161 through line 166. Overhead from column 161 leaves through line 163, is compressed by compressor 164, cooled by an aftercooler 142, and passes through line 163a to join line 125 for recycling to column 141. Bottoms from column 161 are heated by passing through line 167, reboiler 168, and recycle line 169 to column 161. Discharge bottoms leave column 161 through line 165 and become feedstock for product column unit 170.

An overhead stream from column 171 leaves through line 173, and bottoms leave through line 175 and then pass through optional cross exchanger 159, line 176, chiller 172, line 177, pump 174, and line 178 before splitting into a portion going through line 166 to the top of column 161 and the remaining portion passing through line 179 to split into two portions in lines 144 and 154 for respective columns 141 and 151.

The bottoms of column 171 is reboiled via line 177, reboiler 178 and recycle line 179 to column 171. Optionally the physical solvent is stripped with stripping steam via line 217 while the steam condensate is recovered via line 218.

The overhead in line 173 is condensed in still reflux condenser 181 and passes through line 183 to reflux accumulator 185, wherein reflux is separated and passes through line 186 to pump 188 and line 187 to column 171 as reflux at the top thereof and hydrocarbon products are removed from the accumulator 185 through line 189.

Cooling medium such as cooling water or refrigerant enters the process through line 191 and is split into a portion going to optional heat exchanger 128 through line 193 and a portion moving through line 195 to heat exchanger 181. The warm cooling medium leaves through line 197 to be joined by the other portion in line 194 and becomes the combined stream in line 199. Typically, the temperature of the lean solvent in line 183 is warmer than −20° F.

In FIG. 3, the stabilizer unit 160 is slightly different from the stripper unit 30 of FIG. 1 and stripper unit 90 of FIG. 2, in the sense that a small portion of the lean solvent is added as reflux to the top of column 161 via line 166. This affects preferential recovery of desirable hydrocarbons, thereby taking advantage of improved partial pressures of desirable hydrocarbons in column 161. In another aspect, FIG. 3 is different from FIG. 2, wherein the rich solvent stream 145 is flashed in a separate unit 146 and only vapors are subjected to solvent extraction in the secondary extractor unit 150.

Figure 4:
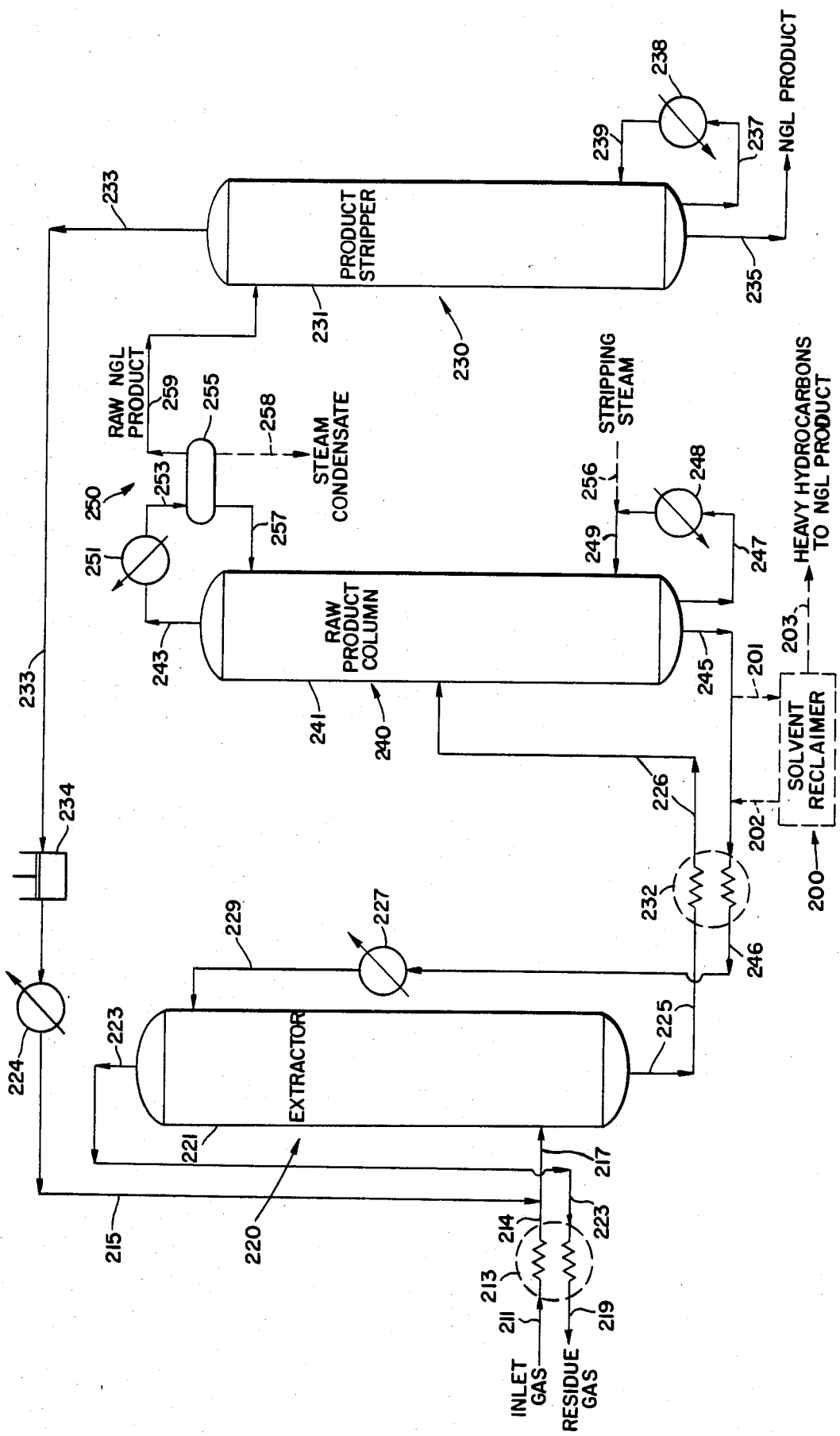
FIG. 4 is a schematic flow sheet for extraction of an inlet gas stream and a recycle gas stream with a preferential physical solvent to produce a liquid product stream and a residue gas stream by using three treating units, with the product stripper and the raw product column being reversed in comparison to the arrangement shown in FIG. 1.

The process shown schematically in the flow sheet of FIG. 4 comprises an extractor unit 220, a raw product unit 240, and a product stripper unit 230. Inlet gas stream 211 enters an optional heat exchanger 213 and becomes cooled inlet gas stream 214 which combines with recycled gas stream 215 to produce combined gases 217 for use as feedstock to extractor unit 220. Depending upon operating temperatures in the extractor column, cooling is supplied within the optional heat exchanger 213 by overhead stream 223 which becomes heated residue gas stream 219, thereby recovering available cooling energy.

After entering column 221 of extractor unit 220 at a pressure which varies between 250–1300 psig, feedstock 217 rises countercurrently to the downward flow of a lean preferential physical solvent stream entering the top of column 221 from line 229 after being cooled in cooler 227. The cooler 227 generally operates such that the temperature of lean solvent in stream 229 is −20° F. or warmer. Overhead stream 223 leaves the top of column 221 for passage to heat exchanger 213. Bottoms in column 221 leave through line 225 to become feedstock for raw product unit 240.

Before entering column 241 of raw product unit 240, bottoms in line 225 passes through optional heat exchanger 232 to become heated bottoms in line 226. The pressure in extractor column 221 is at a pressure in the order of 250–1300 psig, but the pressure in raw product column 241 may be at a lower pressure of the order of 100 to 1300 psig, so that heated bottoms 226 flash when entering column 241.

At the entrance of column 241, heated bottoms in line 226 are further heated by passing through line 247, reboiler 248, and line 249. Overhead leaves through line 243 at the top of column 241, and bottoms leave through line 245 to pass through optional heat exchanger 232 and enter cooler 227 through line 246.

Overhead stream 243 is cooled and condensed in condensing unit 250 and in particular in a partial or total condenser 251 and passes through line 253 to accumulator 255 from which a reflux stream enters column 241 through line 257, and a gas or liquid raw NGL product stream enters product stripper column 231 through line 259.

The flashed gases leave the top of column 231 through line 233, are compressed by compressor 234 and cooled by cooler 224, and pass through line 215 to join the inlet gas in line 214 and become combined feedstock in line 217 for column 221 at the inlet gas pressure. Bottoms of column 231 are recycled through line 237 to reboiler 238 and line 239 for supplying heat to the contents of column 231. Since the vapors leaving in line 233 may contain some desirable components such as propane and ethane, the recycling of line 233 to the inlet to the extractor unit 220 results in improved recoveries of the desirable components.

There are some preferential physical solvents such as mesitylene, mixed xylenes, reformates, and the like which may have lower molecular weight and more relative volatility when compared to some of the absorption lean oils that are used in existing absorption type plants. If some of these gas streams, used as feedstock for the process, contain minor amounts of heavier hydrocarbons in comparison to the proposed preferential physical solvent, these heavier hydrocarbons will tend to build up in the circulating solvent and thus retard the effectiveness of the physical solvent because the final product column would be unable to separate the heavier hydrocarbons from the physical solvent. Therefore, as part of this invention, utilization of solvent reclaimer unit 200 that is shown in FIGS. 1, 2, and 3 can effectively prevent the build up of hydrocarbons in the solvent loop. In order to minimize their impact on solvent selectivity, the hydrocarbon content should be limited to less than 10% by volume and preferably to less than 5%. The volume of slipstream 201 is a function of the proportionate quantity of heavier hydrocarbons in the inlet gas stream and is also simultaneously a function of the quantity of hydrocarbons in the regenerated solvent stream leaving the bottom of the fractionator or regenerator.

As shown in FIGS. 1, 2, and 3, a slip stream of hot lean solvent is sent via line 201 to a solvent reclaimer unit 200 which is operating at low pressures of up to 2 psia but is preferably operating at 5 psig or higher and utilizing external heat to boil off the physical solvent from the mixture and return it to the solvent loop via line 202. The separated hydrocarbons are discharged via line 203 and can be mixed with the NGL product without being detrimental to its gasoline fraction.

Alternatively, the solvent reclaimer section may consist of a fractionating still, if economical to do so as determined by the installation cost versus the reduction in solvent loss along with the heavier hydrocarbons, in order to fractionate the physical solvent in stream 201 from the heavier hydrocarbons. The fractionating still can be designed to minimize the loss of solvent with the heavier hydrocarbons that may end up in the NGL product.

It should be recognized that because the molecular weights of heavier components are generally unknown and cannot be compared to those of the physical solvent, the separation is somewhat difficult in the sense that it may require a large number of theoretical stages, of course balanced by the appropriate amount of reflux. In the final analysis, economics of the process, when weighed against the cost of solvent loss in the product, must be considered.

As an additional alternative to the removal of such heavier hydrocarbon components from the physical solvent, an analysis of the inlet gas in streams 11, 61, or 121 after the optional cooler 13, 63, or 129 may be made to determine if such components can be separated from the vapor stream before contact in the primary extraction units 20, 70, or 149. If so, it may be economically desirable to remove such components by installing a separating vessel after cooler 13, 63, or 129 thereby effectively separating condensed liquids. The vapor portion flows from this separator towards the extraction units 20, 70, or 140 while the separated liquid combines with the hydrocarbon product in streams 59, 119, or 189. If the separated liquid contains some undesirable components such as methane and ethane, the separated liquid may be treated in a relatively mild stripping column, thereby stripping methane and ethane along with minor amounts of $C_3$ and heavier, as long as the stripped vapors do not contain hydrocarbons heavier than the physical solvent. The stripped vapors can be conveniently treated in the stripper units 30, 80, 90, 150, or 160.

EXAMPLE 1

A natural gas processing plant, having the equipment shown in FIG. 3 and using the process described hereinbefore, is operated with lean absorption oil which has a molecular weight of 180, normal boiling point of 460° F. and a gravity of 40° API. The inlet gas stream in line 121 flows at 276 million standard cubic feet per day (MMSCFD) and is at 85° F. It is at 60° F. in line 129 as it enters column 141 which operates at 900 psig. Column 151 operates at 385 psig. Column 161 operates at 260 psig. Column 171 operates at 102 psig.

Lean absorption oil in line 177 is at 50° F. and is split in three ways to provide 1041 gallons per minute (gpm) in line 144, 64 gpm in line 154, and 187 gpm in line 166, totalling 1,292 gpm, to respective columns 141, 151, and 161.

The inlet gas stream contains 142 lb-mole/hr of nitrogen and 266 lb-molehr of $CO_2$. The compositions of the inlet gas stream in line 121, the residue gas stream in line 143, the fuel gas stream in line 153, and the NGL product stream in line 189 are given in Table V.

TABLE V

| Components, in | MATERIAL BALANCE | | | |
|---|---|---|---|---|
| | Stream in Line No. | | | |
| lb-mole/hr | 121 | 143 | 153 | 189 |
| Methane | 25,338 | 24,550 | 788 | 0 |
| Ethane | 2,822 | 2,676 | 136 | 10 |
| Propane | 1,095 | 654 | 35 | 406 |
| $C_4$ Hydrocarbons | 641 | 26 | 1 | 614 |

EXAMPLE 2

The hydrocarbons recovery plant shown in FIG. 3 and utilized for Example 1 is economically rejuvenated by replacing all of its lean absorption oil with one of the preferential physical solvents of this invention, namely mesitylene. The temperature of stream 177 is 50° F. The flow rates of streams 144, 154, and 166 are, respectively, 1,040, 64, and 187 gpm, totalling 1,291 gpm.

The flow rate of inlet gas line 121 is 276 million standard cubic feet per day (MMSCFD), having the same composition shown in Table V. The temperature in line 129 is 60° F., and the pressures in columns 141, 151, 161, and 171 are, respectively, 900, 385, 260, and 102 psig.

The compositions of the inlet gas stream in line 121, the residue gas stream in line 143, the fuel gas stream in line 153, and the NGL product stream in line 189 are summarized in Table VI.

TABLE VI

| Components, in | MATERIAL BALANCE | | | |
|---|---|---|---|---|
| | Stream in Line No. | | | |
| lb-mole/hr | 121 | 143 | 153 | 189 |
| Methane | 25,338 | 24,421 | 917 | 0 |
| Ethane | 2,822 | 2,643 | 171 | 8 |
| Propane | 1,095 | 406 | 30 | 659 |
| $C_4$ Hydrocarbons | 641 | 15 | 2 | 624 |

Thus, by simply substituting the absorption oil of Example 1 with a preferential physical solvent, namely mesitylene, while operating the plant at same conditions, i.e. no changes in physical equipment, propane recovery improved from 37.1% to a surprising level of 60.2%.

EXAMPLE 3

The hydrocarbons recovery plant shown in FIG. 3 and utilized for Example 1 is economically rejuvenated by replacing all of its lean oil with one of the other preferential physical solvents of this invention, namely mixed xylenes. The temperature of stream 177 is 50° F. The flow rates of streams 144, 154, and 166 are, respectively, 1,136, 70, and 205 gpm, totalling 1,411 gpm.

The flow rate of inlet gas line 121 is 276 million standard cubic feet per day (MMSCFD), having the same composition shown in Table V. The temperature in line 129 is 60° F., and the pressures in columns 141, 151, 161, and 171 are, respectively, 900, 385, 280, and 102 psig.

The compositions of the inlet gas stream in line 121, the residue gas stream in line 143, the fuel gas stream in line 153, and the NGL product stream in line 189 are summarized in Table VII.

TABLE VII

| Components, in | MATERIAL BALANCE | | | |
|---|---|---|---|---|
| | Stream in Line No. | | | |
| lb-mole/hr | 121 | 143 | 153 | 189 |
| Methane | 25,338 | 24,233 | 1,105 | 0 |
| Ethane | 2,822 | 2,599 | 214 | 9 |
| Propane | 1,095 | 305 | 35 | 755 |
| $C_4$ Hydrocarbons | 641 | 2 | 0 | 639 |

In this example, replacing the absorber oil with mixed xylenes, a preferential physical solvent for this invention, and increasing the solvent flowrate by only 9.2%, surprisingly improved the propane recovery by 14.6% over the use of mesitylene in Example 2 and also to a level of 68.9% when compared to a level of 37.1% in Example 1, when all other operating conditions are identical. It further illustrates that a mixed xylenes stream is relatively more selective towards propane than mesitylene, both being the preferential physical solvents for this invention process. With an increase of 9.2% solvent flowrate, those skilled in the art of treating natural gas with absorption oil while minimizing ethane recovery would have anticipated an improvement of only about 9.2% in propane recovery, but it was surprisingly 14.6% better, because preferential physical solvents combine their selectivity characteristics with their solubility characteristics. This behavior is contrary to the absorption principle characterizing lean oils, in which solubility is the only parameter.

EXAMPLE IV

A lean oil absorber plant named Santa Rosa and located near Grand Falls, TX was built in the mid-1940's to process natural gas produced by surrounding wells. It was successfully operated for many years by El Paso Natural Gas Co. but was replaced with an adjacent turbo-expander plant by El Paso Hydrocarbons Company, the current owner, in 1981. The turbo-expander plant used the old treating plant for sweetening and partial drying of the inlet natural gas.

In May 1984, after minimal modification, the old absorber plant was put back in operation as a semiworks plant operated as a pilot plant to which dry, sweet inlet natural gas was supplied by the treating plant. The absorber plant was then operated with a preferential physical solvent and according to the Mehra Process with both its NGL product and its natural gas residue product being returned to the turhoexpander plant for further processing. The converted lean oil plant was again shut down in March 1985.

Two preferential physical solvents were used separately in the converted Santa Rosa plant. These solvents were Selexol, a trademark of The Norton Co., and UCC-MP-1, a trademark of Union Carbide Corp. The former solvent was a mixture of dialkyl ethers of polyalkylene glycol. The latter solvent was understood to fit within the required parameters for a preferential physical solvent. The gas flowrate in the tests varied from 2.25 to 6.85 MMSCFD. The solvent flowrates varied from 75 to 280 gpm. The final flash pressures were 9–30 psia. The final flash temperatures were 90° to 250° F. The absorber pressure was 565 to 650 psig. An additional objective of this demonstration plant was to determine the capability of utilizing existing equipment in place, capability being measured in terms of percent recovery of hydrocarbons at fixed solvent flowrates. Recoveries were approximately as follows, as averages for both solvents and as percentages of each hydrocarbon component in the inflowing gas:
Ethane: 55%
Propane: 88%
Butanes: 94%
Gasolines: 98%

It was additionally ascertained that (1) no foaming occurred, (2) operation was stable and easy, (3) NGL's were continuously produced, (4) the existing equipment could be utilized, (5) energy requirements were lower than for lean oil operation, and (6) operation was characterized by increased reliability and longer on-stream time than while running with lean oil as solvents. It was clearly established that the utilization of existing equipment in-place was satisfactory with minimum modifications, while utilizing preferential physical solvents to recover the desired hydrocarbon components at much higher levels than those indicated for absorber plants in Table I.

It should be understood from the preceding four examples and the preceding description that the process of this invention can economically rejuvenate an old absorber plant without modification of the apparatus and simply by substitution of one solvent for another. However, it is realistic to assume that pumps will be found to need new seals, trays in the absorber column will be found to be outmoded by newer designs, or one unit operation will have been found by experience to have been a bottleneck or will be ascertained by computer simulation to be inefficient with the new solvent. In such situations, a reasonable amount of plant retrofit should be expected, reasonable being interpreted as within the limitations of economic practicality, maximization of efficiency and profits, and the like.

Such retrofit can even include replacement of an entire column if such economic criteria are met, as in an absorption process for the removal of $C_{2+}$ hydrocarbons from a natural gas stream by absorbing the $C_{2+}$ hydrocarbons with a lean oil to produce a residue gas stream of pipeline quality and a rich solvent from which the $C_{2+}$ hydrocarbons are recovered and wherein a need exists for recovering at maximum recoveries a selected hydrocarbon component and heavier hydrocarbons within the group consisting of ethane, propane, butane, and pentane without the need simultaneously to recover hydrocarbons lighter than the selected hydrocarbon component from the natural gas stream, the selected component being ethane, propane, or butane, and for recovering to a selected degree the hydrocarbon lighter than the selected hydrocarbon component when the lighter hydrocarbon is ethane or propane.

In such a situation, the process of this invention improves the hydrocarbon recovery process by substituting for the lean oil an extractant which is a preferential physical solvent and is selective for ethane and heavier hydrocarbon components of the inlet gas stream such that the relative volatility of methane over ethane is at least 6.0 and the solubility of ethane in the solvent is at least 1.0 standard cubic foot of ethane per gallon of the extractant or the preferential factor is at least 6.0.

It should also be understood that the process of this invention lends itself to the use of waste heat recovery, quite contrary to the other state-of-the art processes that are capable of recovering ethane and propane under high recovery levels. Similarly, the opportunity for integrating heat exchangers is extensive. Even though FIG. 1 indicates units 13, 32, 27, 38, 48, and 51, FIG. 2 shows units 63, 77, 92, 98, 108, and 111, and FIG. 3 contains units 122, 128, 172, 159, 168, 215, and 181, any combination of waste heat exchange, rich/lean solvent heat exchange, steam stripping in lieu of the product column reboiler, and additional side reboiling for columns 21, 31, 41, 71, 91, 101, 141, 151, 161, and 171 are to be understood as part of this invention process with the objective of maximizing the recovery of hydrocarbons under given economic criteria.

Because it will be readily apparent to those skilled in the art of treating natural gas that innumerable variations, modifications, applications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. In an absorption process for the removal of $C_{2+}$ hydrocarbons from a natural gas stream by absorbing said $C_{2+}$ hydrocarbons with a lean oil to produce a residue gas stream of pipeline quality and a rich oil from which the $C_{2+}$ hydrocarbons are recovered, the improvement which comprises providing the capability, within existing equipment after reasonable retrofit thereof of selectively extracting said $C_{2+}$ hydrocarbons from said gas stream with a lean preferential physical solvent according to said maximum recoveries and to said selected degree of (a) ethane in amounts ranging up to 95%, (b) propane in amounts ranging up to 100%, (c) butane in amounts ranging up to 100%, or (d) pentanes and hihger molecular weight hydrocarbons in amounts ranging up to 100% by:

A. selecting an absorber plant, having said existing equipment, which is used for recovering maximum quantities of said $C_{2+}$ hydrocarbons from said gas stream while using lean oils as solvent for said $C_{2+}$ hydrocarbons;

B. selecting a preferential physical solvent which is selective for ethane and heavier hydrocarbon components of said gas stream such that the relative volatility of methane over ethane is at least 6.0 and the solubility of ethane in said solvent is at least 1.0 standard cubic foot of ethane per gallon of said solvent or the preferential factor is at least 6.0;

C. replacing said oils in said selected absorber plant with a selected volume of said selected preferential physical solvent; and D. while using said equipment in extraction mode, contacting said gas stream with said lean preferential physical solvent at a selected flow rate within the range of 0.001–0.5 gallon of lean solvent per standard cubic foot of said gas stream to produce a residue gas stream of pipeline specifications and a rich solvent stream containing said ethane and heavier hydrocarbon components.

2. The process of claim 1, wherein said contacting in said Step D is at 250–1300 psig and wherein said flow rate of said preferential physical solvent in said Step D is selectively adjusted in response to market conditions.

3. The process of claim 2, wherein said gas stream is selected from the group consisting of:

A. natural gas at up to saturation with water;

B. sweet natural gas;

C. dry natural gas; and

D. sour natural gas which is pre-sweetened in gas phase with an aqueous amine solution and dried with an aqueous glycol solution.

4. The process of claim 3 which further comprises the following steps:

A. distilling said hydrocarbon-containing solvent steam to produce a stream of lean preferential physical solvent and a hydrocarbon-containing raw NGL product stream;

B. selectively flashing or stripping said raw NGL product stream to produce:
(1) a gas fraction for recycling and
(2) an NGL product stream of said selected hydrocarbon component and said heavier hydrocarbon components as a product while recovering said lighter hydrocarbons only to said selected degree.

5. The process of claim 3, wherein said contacting in said Step D with said lean preferential physical solvent occurs in successive contacting steps in combination with a flashing step.

6. The process of claim 5, wherein said lean preferential physical solvent is split into a major portion and a remaining portion, said major portion being fed to the top of a primary extractor column and said remaining portion being fed to the top of a secondary extractor column in which relative concentrations of desirable hydrocarbons are significantly higher than relative concentrations thereof in said primary extractor column, said primary extractor column producing a rich solvent bottoms stream containing hydrocarbons that are at least partially fed to said secondary extractor column.

7. The process of claim 6, wherein said rich solvent bottoms stream is fed to said secondary extractor column and said flashing step occurs internally of said secondary extractor column to produce flashed gases which rise countercurrently to said remaining portion of said lean solvent.

8. The process of claim 7, wherein said secondary extractor column produces a second bottoms stream which is fed to a column having a reboiler and producing a recycle gas stream and a solvent stream consisting essentially of said selected hydrocarbon component and said heavier hydrocarbon components as a product.

9. The process of claim 6, wherein said flashing step occurs externally of said secondary extractor column to produce flashed gases which are fed to said secondary extractor column for extraction with said remaining portion of said lean solvent.

10. The process of claim 9, wherein said flashing step produces a first bottoms stream and said secondary extractor column additionally produces a second bottoms stream, said first and second bottoms streams being joined to form a combined solvent stream which is fed to a column having a reboiler and producing a recycle gas stream and a solvent stream consisting essentially of said selected hydrocarbon component and said heavier hydrocarbon components as a product.

11. The process of claim 3, wherein said relative volatility is at least 7.0.

12. The process of claim 3, wherein said relative volatility is at least 8.0.

13. The process of claim 3, wherein said relative volatility is at least 6.5, said solubility is at least 2.0, and said preferential factor is at least 13.0.

14. The process of claim 3, wherein said relative volatility is at least 7.0, said solubility is at least 2.75, and said preferential factor is at least 19.25.

15. The process of claim 3 which further comprises the following steps:

A. selectively flashing or stripping said rich solvent stream to produce a gas fraction for recycling and a hydrocarbon-containing solvent stream; and B. distilling said hydrocarbon-containing solvent stream to produce a stream of lean preferential physical solvent and a stream of a selected hydrocarbon component and heavier hydrocarbon components as a product while recovering hydrocarbons lighter than said selected hydrocarbon component, when said selected hydrocarbon component is ethane and/or propane, only to said selected degree.

16. The process of claim 1, wherein said preferential physical solvent is selected from the group consisting of dialkyl ethers of polyalkylene glycol, mesitylene, and reformate streams and crackate streams that are rich in monocyclic $C_8$–$C_{10}$ aromatic compounds having methyl, ethyl, or propyl aliphatic groups, including mesitylene, n-propyl benzene, n-butyl benzene, o-xylene, m-xylene, p-xylene, and mixtures thereof.

17. The process of claim 16, wherein said preferential physical solvent is substantially pure mesitylene.

18. A process for economic rejuvenation of a lean oil absorber plant by conversion thereof to an extraction plant, comprising the following steps:

A. selecting an absorber plant having existing equipment which is suitable for such conversion and is usable for recovering maximum quantities of $C_2+$ hydrocarbons from a gas stream while using lean oils as solvent for said $C_2+$ hydrocarbons;

B. selecting a preferential physical solvent which is selective for ethane and heavier hydrocarbon components of said gas stream such that the relative volatility of methane over ethane is at least 6.0 and the solubility of ethane in said solvent is at least 1.0 standard cubic foot of ethane per gallon of solvent;

C. replacing said lean oils in said selected absorber plant with a selected volume of said selected preferential physical solvent;

D. providing the capability, within said existing equipment, of selectively extracting said $C_2+$ hydrocarbons from said gas stream with said preferential physical solvent according to said selected degree of (a) ethane in amounts ranging up to 70%, (b) propane in amounts ranging up to 95%, (c) butane in amounts ranging up to 98%, or (d) pentanes and higher molecular weight hydrocarbons in amounts ranging up to 99%;

E. while using said equipment in extraction mode, contacting said gas stream with said preferential physical solvent at a selected flow rate within the range of 0.001-0.5 gallon of lean solvent per standard cubic foot of said gas stream to produce a residue gas stream of pipeline specifications and a rich solvent stream containing said ethane and heavier hydrocarbon components, F. selectively flashing or stripping said rich solvent stream to produce a gas fraction for recycling and a hydrocarbon-containing solvent stream; and G. distilling said hydrocarbon-containing solvent stream to produce a stream of said preferential physical solvent and a stream of said selected hydrocarbon component and said heavier hydrocarbon components as a product, whereby said absorber plant operates as an extraction plant and the yield of propane is increased to at least 95% when a minimum amount of said ethane is rejected and up to 70% when a maximum amount of said ethane is rejected, so that said extraction plant operates profitably and is economically rejuvenated.

19. A process for economic rejuvenation of an existing lean oil absorber plant for treating a stream of natural gas, wherein said lean oil plant has been under-utilized and comprises an absorber column which is undersized in relation to the remainder of said plant and is likely to become flooded if said plant should reach full production, said process comprising:

A. replacing said absorber column with a larger column that is designed to accept the maximum solvent flow rate for which said remainder of said plant is designed;

B. providing the capability for said absorber plant of selectively extracting said $C_{2+}$ hydrocarbons from said gas stream with a lean preferential physical solvent according to said maximum recoveries and to said selected degree of (a) ethane in amounts ranging up to 70%, (b) propane in amounts ranging up to 95%, (c) butane in amounts ranging up to 98%, or (d) pentanes and higher molecular weight hydrocarbons in amounts ranging up to 99% by:

(1) selecting a preferential physical solvent which is selective for ethane and heavier hydrocarbon components of said gas stream such that the relative volatility of methane over ethane is at least 6.0 and the solubility of ethane in said solvent is at least 1.0 standard cubic foot of ethane per gallon of said solvent or the preferential factor is at least 6.0;

(2) replacing said lean oils in said selected absorber plant with a selected volume of said selected preferential physical solvent; and (3) while using said equipment in extraction mode, contacting said gas stream with said lean preferential physical solvent at a selected flow rate within the range of 0.001-0.5 gallon of lean solvent per standard cubic foot of said gas stream to produce a residue gas stream of pipeline specifications and a rich solvent stream containing said ethane and heavier hydrocarbon components.

20. In an absorption process for the removal of $C_{2+}$ hydrocarbons from a natural gas stream by absorbing said $C_{2+}$ hydrocarbons with a lean oil to produce a residue gas stream of pipeline quality and a rich solvent from which the $C_{2+}$ hydrocarbons are recovered, the improvement which comprises utilizing a preferential physical solvent which is selective for ethane and heavier hydrocarbon components of said gas stream such that the relative volatility of methane over ethane is at least 6.0 and the solubility of ethane in said solvent is at least 1.0 standard cubic foot of ethane per gallon of said preferential physical solvent or the preferential factor is at least 6.0 and operating said absorption process as an extraction process for selectively extracting said ethane and heavier components from said natural gas stream.

21. The process of claim 20, wherein said extraction is at 250-1300 psig and wherein said flow rate of said preferential physical solvent is selectively adjustable.

22. The process of claim 21, wherein said gas stream is selected from the group consisting of:

A. natrual gas at up to saturation with water;
B. sweet natural gas;
C. dry natural gas; and
D. sour natural gas which is pre-sweetened in gas phase with an aqueous amine solution and dried with an aqueous glycol solution.

23. The process of claim 22 which further comprises the following steps:

A. selectively flashing or stripping said rich solvent stream to produce a gas fraction for recycling and a hydrocarbon-containing solvent stream; and B. distilling said hydrocarbon-containing solvent stream to produce a stream of lean preferential physical solvent and a stream of a selected hydrocarbon component and heavier hydrocarbon components as a product while recovering hydrocarbons lighter than said selected hydrocarbon component, when said selected hydrocarbon component is ethane or propane, only to said selected degree.

24. The process of claim 23, wherein said lean preferential physical solvent from said step B of claim 23 is cooled before recycling to said extracting of claim 20 as said physical solvent.

25. The process of claim 23, wherein said rich solvent is heated by lean/rich solvent heat exchanging.

26. The process of claim 20, wherein said preferential physical solvent is selected from the group consisting of dialkyl ethers of polyalkylene glycols, hemimellitene, pseudocumene, mesitylene, cumene, 1,2-methylethylbenzene. 1,3-methylethylbenzene, 1,4-methylethylbenzene, alkyl substituted monocyclic $C_8$-$C_{10}$ aromatic hydrocarbons, mixtures of said hydrocarbons, and reformate streams and crackate streams that are rich in monocyclic $C_8$-$C_{10}$ aromatic compounds having methyl, ethyl, or propyl aliphatic groups, including mesitylene, n-propyl benzene, n-butyl benzene, o-xylene, m-xylene, p-xylene, and mixtures thereof.

27. The process of claim 26, wherein said preferential physical solvent is substantially pure mesitylene.

28. The process of claim 26, wherein said $C_8$-$C_{10}$ aromatic streams are catalytically reformed naphthas in which a $C_9$ heart cut is enriched in $C_9$ alkylbenzenes.

29. The process of claim 26, wherein said preferential physical solvent is selected from the group consisting of $C_9$ alkylaromatics, a $C_7$ to $C_9$ mixture of alkylaromatics, and a $C_8$-$C_{10}$ mixture of alkylaromatics.

30. The process of claim 29, wherein said preferential physical solvent is selected from the group consisting of $C_7$ aromatics, $C_8$ aromatics, $C_9$ aromatics, and mixtures thereof.

31. The process of claim 29, wherein said $C_8$-$C_{10}$ aromatic streams are $C_9$ alkylaromatics derived from conversion of methanol to gasoline.

32. The process of claim 29, wherein said $C_8$-$C_{10}$ aromatic streams are $C_9$ alkylaromatics derived from conversion of syngas to gasoline.

33. The process of claim 29, wherein said $C_8$-$C_{10}$ aromatic streams are $C_9$ alkylaromatics derived from pyrolysis of coal to produce coke.

34. The process of claim 29, wherein said $C_8$-$C_{10}$ aromatic streams are alkylaromatic streams which contain substantial quantities of alkylbenzenes and are produced by petroleum processing operations selected from the group consisting of transalkylation, isomerization, and disproportionation.

35. The process of claim 34, wherein said alkylaromatic streams are mixed xylenes.

36. The process of claim 26, wherein said Preferential physical solvent has an initial boiling point of 230°-280° F., an end boiling point range of 350°-425° F., and an API gravity of 35-60.

37. The process of claim 20, wherein additional selectivity is provided by using a reboiler and a stripping section in an extraction column for selectively extracting and stripping said gas stream with said preferential physical solvent, thereby gaining an additional degree of freedom.

38. The process of claim 37, wherein said additional degree of freedom is effectively utilized by appropriately selecting the reboiling temperature at the bottom of said column in order to produce said rich solvent stream consisting essentially of only economically desirable hydrocarbons out of said ethane and heavier hydrocarbon components, thereby rejecting economically undesirable hydrocarbon components.

39. The process of claim 38, wherein a stream of said rejected undesirable hydrocarbon components, flowing upwardly through said stripping section of said column, contains some desirable hydrocarbons which are recovered preferentially by mass transfer principles by transfer to said physical solvent.

40. The process of claim 38, wherein said rejected hydrocarbons, stripped from said rich solvent, leave said stripping section of said column and join the incoming natural gas stream to form a combined stream which flows upwardly in said extraction section of said column, wherein said lean solvent preferentially recovers any contained desired hydrocarbons.

41. The process of claim 39, wherein said rich solvent leaving the bottom of said column is let down in the pressure to a pressure level that is consistent with the operation of a distillation column for conducting said distilling of said hydrocarbon-containing solvent stream to produce a stream of lean preferential physical solvent and a stream of a selected hydrocarbon component and heavier hydrocarbon components as a product while recovering hydrocarbons lighter than said selected hydrocarbon component, when said selected hydrocarbon component is ethane or propane, only to said selected degree.

42. The process of claim 41, wherein said rich solvent is heated before entering said distillation column in order to lower the reboiler heat load on said distillation column.

43. In an absorption process for treating a gas stream containing methane, $C_2+$ hydrocarbons, and an inert gas with a lean oil for recovering at least a portion of said $C_2+$ hydrocarbons, an improvement comprising:

A. selecting a preferential physical solvent which is selective for a selected component of said $C_2+$ hydrocarbons of said gas stream such that the relative volatility of methane over ethane is at least 6.0 and the solubility of ethane in said solvent is at least 1.0 standard cubic foot of ethane per gallon of solvent or the preferential factor is at least 6.0;

B. replacing said lean oil with a selected volume of said selected preferential physical solvent;

C. providing the capability of selectively extracting said $C_2+$ hydrocarbons from said gas stream with said preferential physical solvent according to a selected degree of (a) ethane in amounts ranging up to 95%, (b) propane in amounts ranging up to 100%, (c) butane in amounts ranging up to 100%, or (d) pentanes and higher molecular weight hydrocarbons in amounts ranging up to 100%;

D. selectively extracting said gas stream with said preferential physical solvent at a selected flow rate within the range of 0.001-0.5 gallon of lean solvent per standard cubic foot of said gas stream to produce a residue gas stream of pipeline specifications and a rich solvent stream containing said selectively extracted $C_2+$ hydrocarbons;

E. selectively flashing or stripping said rich solvent stream to produce a gas fraction for recycling and a hydrocarbon-containing solvent stream; and F. distilling said hydrocarbon-containing solvent stream to produce a stream of said preferential physical solvent and a stream of said selected and heavier hydrocarbon components as a product, whereby said absorption process operates as an extraction process and the yield of propane is increased to at least 95% when a minimum amount of said ethane is rejected and up to 70% when a maximum amount of said ethane is rejected.

44. The process of claim 43, wherein said extracting step is at 250-1300 psig and wherein said flow rate of said preferential physical solvent is selectively adjustable.

45. The process of claim 43, wherein said gas stream is selected from the group consisting of:

A. natural gas at up to saturation with water;
B. sweet natural gas;
C. dry natural gas; and
D. sour natural gas which is pre-sweetened in gas phase with an aqueous amine solution and dried with an aqueous glycol solution.

46. The process of claim 43, wherein said preferential physical solvent is selected from the group consisting of dialkyl ethers of polyalkylene glycol, mesitylene, and reformate streams and crackate streams that are rich in monocyclic $C_8$-$C_{10}$ aromatic compounds having methyl, ethyl, or propyl aliphatic groups, including mesitylene, n-propyl benzene, n-butyl benzene, o-xylene, m-xylene, p-xylene, and mixtures thereof.

47. The process of claim 43, wherein said preferential physical solvent is substantially pure mesitylene.

* * * * *

UNITED STATES PATENT AND TRADEMARK OFFICE
CERTIFICATE OF CORRECTION

PATENT NO. : 4,696,688
DATED : September 29, 1987
INVENTOR(S) : Yuv R. Mehra

It is certified that error appears in the above-identified patent and that said Letters Patent is hereby corrected as shown below:

IN THE SPECIFICATION:

Column 4, line 12, change "laroe" to --large--.
Column 6, line 64, change "admiXture" to --admixture--.
Column 7, line 20, change "thane" to --ethane--.
Column 23, line 27, change "lb-molehr" to --lb-mole/hr--.

IN THE CLAIMS:

Claim 1, column 26, line 57, change "hihger" to --higher--.
Claim 1, column 27, line 4, change "said oils" to --said lean oils--.
Claim 18, column 28, line 56, change "for said" to --for a--.

Signed and Sealed this

Fifteenth Day of March, 1988

Attest:

DONALD J. QUIGG

Attesting Officer

Commissioner of Patents and Trademarks